Figure 1A:
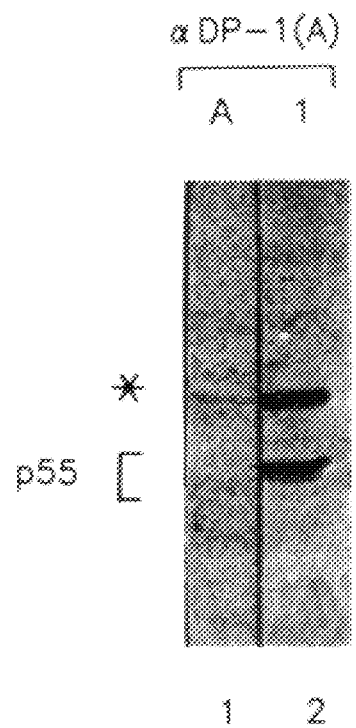

United States Patent [19]

La Thangue

[11] Patent Number: 5,871,901
[45] Date of Patent: Feb. 16, 1999

[54] ASSAY FOR INHIBITORS OF DP-1 AND OTHER DP PROTEINS

[75] Inventor: Nicholas Berrie La Thangue, London, United Kingdom

[73] Assignee: Medical Research Council, London, United Kingdom

[21] Appl. No.: 602,846

[22] PCT Filed: Jul. 3, 1995

[86] PCT No.: PCT/GB95/01567

§ 371 Date: Feb. 26, 1996

§ 102(e) Date: Feb. 26, 1996

[87] PCT Pub. No.: WO96/01425

PCT Pub. Date: Jan. 18, 1996

[30] Foreign Application Priority Data

Jul. 1, 1994 [GB] United Kingdom .................. 9413327

[51] Int. Cl.[6] ...................................... C12S 9/12
[52] U.S. Cl. ................... 435/4; 435/15; 435/21; 435/29; 435/194; 435/375; 530/358; 530/388.24; 530/389.2
[58] Field of Search ...................... 435/375, 194, 435/4, 15, 21, 29; 530/388.24, 358, 389.2

[56] References Cited

FOREIGN PATENT DOCUMENTS

WO 94/10307  5/1994  WIPO .
WO 94/18324  8/1994  WIPO .

OTHER PUBLICATIONS

The Embo Journal vol. 13, No. 13 pp 3104–3114, 1994 Bandara et al "DP–1: a cell cycle–regulated and phosphorylated..".

Oncogens (1995) 10, 1529–1536 Jooss et al "Proto–oncogenic properties of the DP family of proteins".

A Protein Phosphorylation: A Practical Approach—D.G. Hardie, IRL Press (at Oxford University Press), 1993 (pp 126–9, 140–3, 154–5, 202–9, 214–9, 242–5, 278–283).

Krek et al (Cell, 1994, 78 (Jul. 15, 1994) 161–172).

Dynlacht, et al (Genes in Development, 1994 8; 1772–1786.

*Primary Examiner*—Frank C. Eisenschenk
*Assistant Examiner*—Patrick J. Nolan
*Attorney, Agent, or Firm*—Nixon & Vanderhye, P.C.

[57] ABSTRACT

The protein DP-1, part of the DP-1/E2F-1 transcription factor complex, as well as DP-2 and DP-3 has its phosphorylation level regulated during cell cycle progression. This finding allows assays to be based on changes in phosphorylation of DP proteins, in particular for agents which may affect the phosphorylation state of DP. DP-1 has been found to have a greater affinity to DNA when in a hypophosphorylated state. Antibodies that recognize phosphorylation sites on DP-1 are also disclosed.

12 Claims, 9 Drawing Sheets

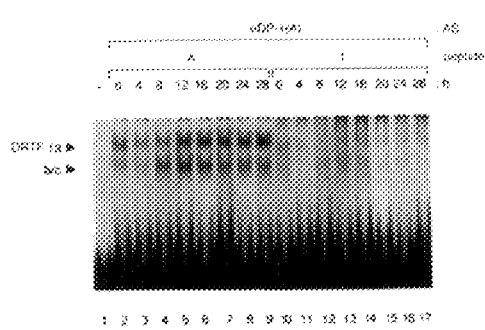
Fig. 2A
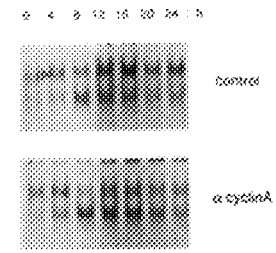
Fig. 2B
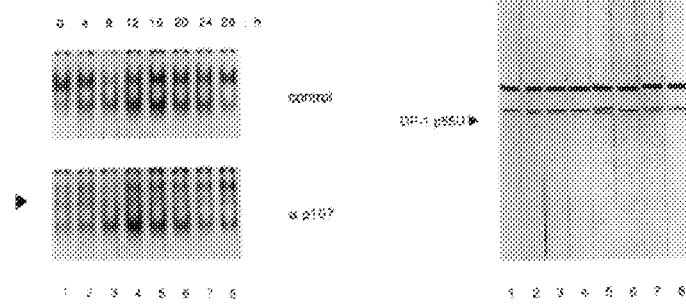
Fig. 2C
Fig. 2D
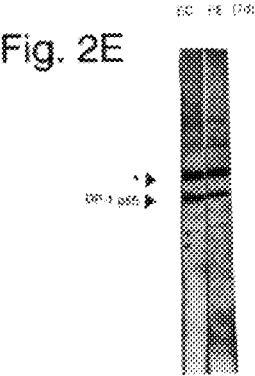
Fig. 2E

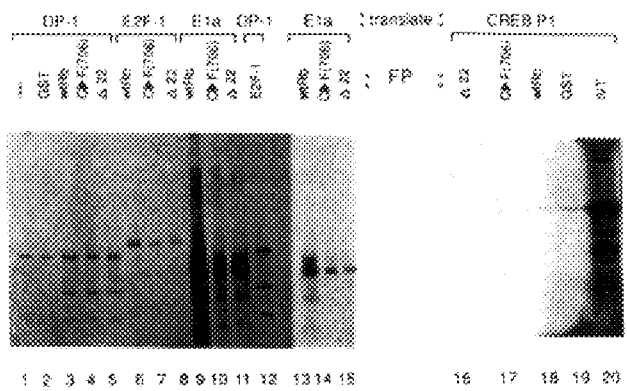
FIG.4A
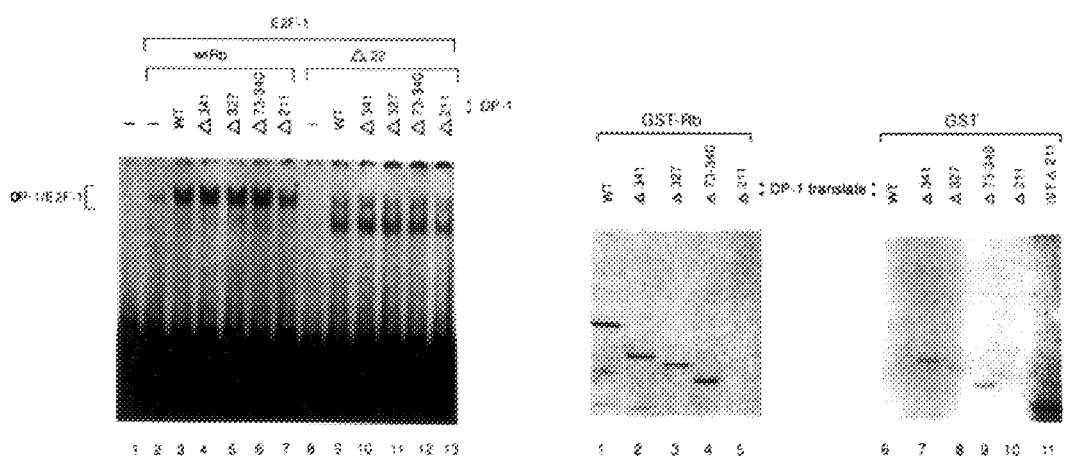
FIG.4B
FIG.4C

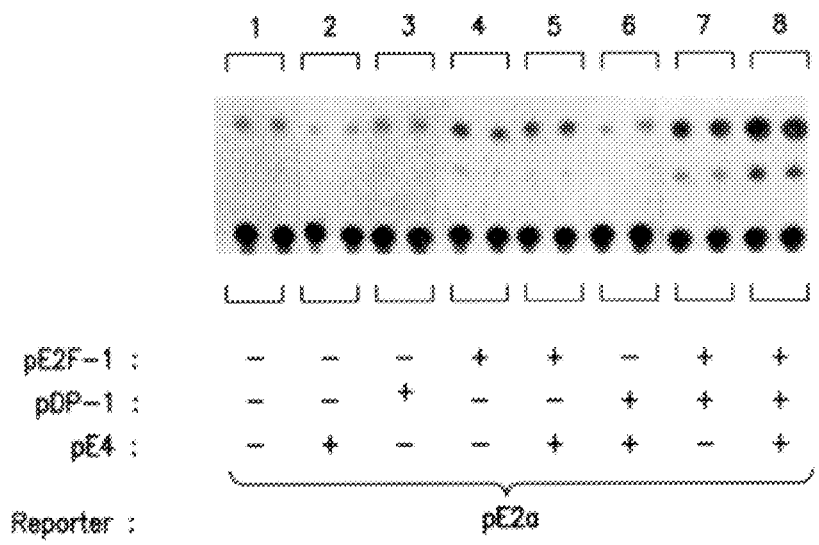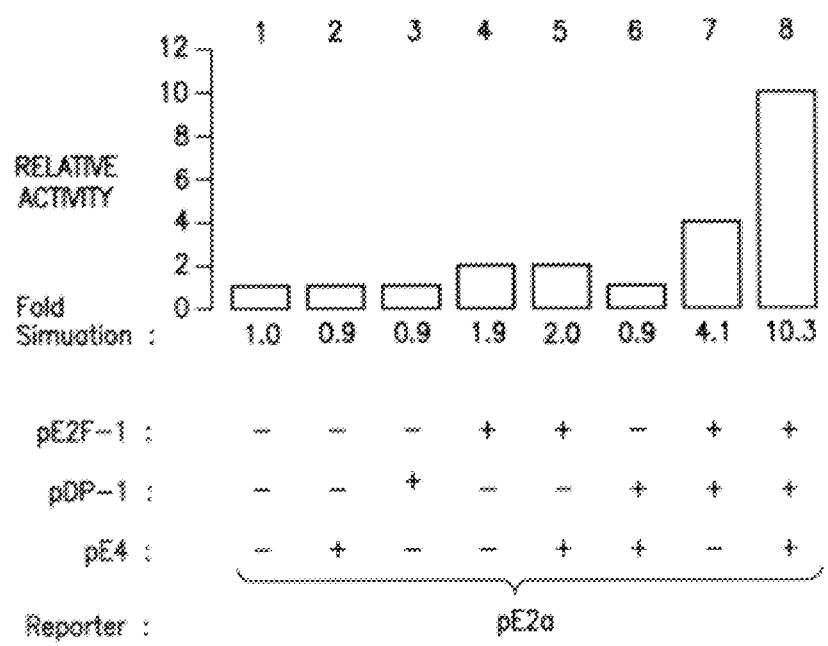
Fig.7A
Fig.7B
Fig.7C

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
    ( A ) LENGTH: 1700 base pairs
    ( B ) TYPE: nucleic acid and encoded amino acids
    ( C ) STRANDEDNESS: double
    ( D ) TOPOLOGY: linear ( i i ) MOLECULE TYPE: cDNA ( x i ) SEQUENCE DESCRIPTION: SEQ ID NO: 1:

```
GTTTCTTCTG  TGGAGGGTAC  GCAGTTAAAG  CCTTGATTTC  CTGGATCTGG  TAAC  ATG                  57
                                                                  Met
                                                                  1

GCA  AAA  GAT  GCC  AGT  CTA  ATT  GAA  GCC  AAC  GGA  GAA  CTA  AAG  GTC  TTT        105
Ala  Lys  Asp  Ala  Ser  Leu  Ile  Glu  Ala  Asn  Gly  Glu  Leu  Lys  Val  Phe
               5                        10                       15

ATA  GAC  CAG  AAT  CTT  AGT  CCT  GGG  AAA  GGT  GTG  GTA  TCT  CTT  GTA  GCC        153
Ile  Asp  Gln  Asn  Leu  Ser  Pro  Gly  Lys  Gly  Val  Val  Ser  Leu  Val  Ala
               20                       25                       30

GTC  CAC  CCG  TCC  ACA  GTC  AAC  ACA  CTT  GGG  AAG  CAG  CTT  TTG  CCA  AAA        201
Val  His  Pro  Ser  Thr  Val  Asn  Thr  Leu  Gly  Lys  Gln  Leu  Leu  Pro  Lys
          35                       40                       45

ACC  TTC  GGA  CAG  TCC  AAT  GTC  AAT  ATC  ACA  CAG  CAA  GTG  GTG  ATT  GGC        249
Thr  Phe  Gly  Gln  Ser  Asn  Val  Asn  Ile  Thr  Gln  Gln  Val  Val  Ile  Gly
50                       55                       60                            65

ACG  CCT  CAG  AGA  CCG  GCA  GCA  TCC  AAC  ACT  ATT  GTG  GTA  GGA  AGC  CCA        297
Thr  Pro  Gln  Arg  Pro  Ala  Ala  Ser  Asn  Thr  Ile  Val  Val  Gly  Ser  Pro
               70                       75                       80

CAC  ACT  CCC  AAC  ACG  CAT  TTT  GTG  TCA  CAG  AAC  CAG  ACG  TCT  GAC  TCC        345
His  Thr  Pro  Asn  Thr  His  Phe  Val  Ser  Gln  Asn  Gln  Thr  Ser  Asp  Ser
               85                       90                       95

TCA  CCT  TGG  TCT  GCT  GGG  AAG  CGG  AAC  AGG  AAG  GGC  GAG  AAG  AAT  GGC        393
Ser  Pro  Trp  Ser  Ala  Gly  Lys  Arg  Asn  Arg  Lys  Gly  Glu  Lys  Asn  Gly
          100                      105                      110

AAG  GGC  CTG  CGG  CAT  TTC  TCC  ATG  AAG  GTG  TGT  GAG  AAG  GTG  CAG  AGG        441
Lys  Gly  Leu  Arg  His  Phe  Ser  Met  Lys  Val  Cys  Glu  Lys  Val  Gln  Arg
     115                      120                      125

AAA  GGA  ACC  ACC  TCC  TAC  AAT  GAG  GTG  GCT  GAC  GAG  CTG  GTG  GCA  GAG        489
Lys  Gly  Thr  Thr  Ser  Tyr  Asn  Glu  Val  Ala  Asp  Glu  Leu  Val  Ala  Glu
130                      135                      140                           145

TTC  AGC  GCT  GCC  GAC  AAC  CAC  ATT  CTA  CCA  AAC  GAA  TCA  GCT  TAT  GAC        537
Phe  Ser  Ala  Ala  Asp  Asn  His  Ile  Leu  Pro  Asn  Glu  Ser  Ala  Tyr  Asp
                    150                      155                      160

CAG  AAG  AAC  ATC  CGG  CGG  CGT  GTC  TAC  GAT  GCC  TTA  AAT  GTG  CTA  ATG        585
Gln  Lys  Asn  Ile  Arg  Arg  Arg  Val  Tyr  Asp  Ala  Leu  Asn  Val  Leu  Met
               165                      170                      175

GCC  ATG  AAC  ATC  ATC  TCC  AAG  GAG  AAG  AAG  GAG  ATC  AAA  TGG  ATC  GGC        633
Ala  Met  Asn  Ile  Ile  Ser  Lys  Glu  Lys  Lys  Glu  Ile  Lys  Trp  Ile  Gly
               180                      185                      190

CTG  CCC  ACC  AAC  TCA  GCT  CAG  GAG  TGC  CAG  AAC  TTA  GAG  GTG  GAG  AGG        681
Leu  Pro  Thr  Asn  Ser  Ala  Gln  Glu  Cys  Gln  Asn  Leu  Glu  Val  Glu  Arg
     195                      200                      205

CAG  AGG  AGG  CTG  GAG  AGG  ATC  AAA  CAG  AAG  CAG  TCT  CAG  CTC  CAG  GAG        729
Gln  Arg  Arg  Leu  Glu  Arg  Ile  Lys  Gln  Lys  Gln  Ser  Gln  Leu  Gln  Glu
210                      215                      220                           225
```

| | | | | | | | | | | | | | | | | |
|---|---|---|---|---|---|---|---|---|---|---|---|---|---|---|---|---|
| CTC | ATC | CTG | CAG | CAA | ATT | GCC | TTC | AAG | AAC | TTG | GTG | CAG | AGA | AAT | CGC | 777 |
| Leu | Ile | Leu | Gln | Gln | Ile | Ala | Phe | Lys | Asn | Leu | Val | Gln | Arg | Asn | Arg | |
| | | | 230 | | | | | 235 | | | | | | 240 | | |
| CAA | GCT | GAG | CAG | CAG | GCC | CGC | AGG | CCG | CCT | CCT | CCC | AAC | TCT | GTC | ATC | 825 |
| Gln | Ala | Glu | Gln | Gln | Ala | Arg | Arg | Pro | Pro | Pro | Pro | Asn | Ser | Val | Ile | |
| | | | 245 | | | | | 250 | | | | | 255 | | | |
| CAC | TTG | CCC | TTC | ATC | ATT | GTC | AAC | ACC | AGC | AGG | AAG | ACA | GTC | ATT | GAC | 873 |
| His | Leu | Pro | Phe | Ile | Ile | Val | Asn | Thr | Ser | Arg | Lys | Thr | Val | Ile | Asp | |
| | | 260 | | | | | 265 | | | | | 270 | | | | |
| TGC | AGC | ATC | TCC | AAT | GAC | AAA | TTT | GAG | TAT | CTG | TTT | AAC | TTT | GAC | AAC | 921 |
| Cys | Ser | Ile | Ser | Asn | Asp | Lys | Phe | Glu | Tyr | Leu | Phe | Asn | Phe | Asp | Asn | |
| | 275 | | | | 280 | | | | | 285 | | | | | | |
| ACG | TTT | GAG | ATC | CAC | GAT | GAC | ATT | GAG | GTG | CTC | AAG | CGC | ATG | GGC | ATG | 969 |
| Thr | Phe | Glu | Ile | His | Asp | Asp | Ile | Glu | Val | Leu | Lys | Arg | Met | Gly | Met | |
| 290 | | | | 295 | | | | 300 | | | | | | 305 | | |
| GCA | TGT | GGG | CTG | GAG | TCT | GGC | AAC | TGC | TCT | GCT | GAA | GAC | CTC | AAG | GTG | 1017 |
| Ala | Cys | Gly | Leu | Glu | Ser | Gly | Asn | Cys | Ser | Ala | Glu | Asp | Leu | Lys | Val | |
| | | | | 310 | | | | 315 | | | | | 320 | | | |
| GCC | AGA | AGT | TTG | GTA | CCA | AAA | GCT | CTA | GAA | CCA | TAC | GTG | ACA | GAA | ATG | 1065 |
| Ala | Arg | Ser | Leu | Val | Pro | Lys | Ala | Leu | Glu | Pro | Tyr | Val | Thr | Glu | Met | |
| | | | 325 | | | | | 330 | | | | | 335 | | | |
| GCT | CAG | GGA | TCC | ATT | GGT | GGC | GTA | TTC | GTC | ACG | ACA | ACA | GGT | TCT | ACA | 1113 |
| Ala | Gln | Gly | Ser | Ile | Gly | Gly | Val | Phe | Val | Thr | Thr | Thr | Gly | Ser | Thr | |
| | | | 340 | | | | | 345 | | | | | 350 | | | |
| TCC | AAT | GGC | ACA | AGG | CTT | TCT | GCC | AGT | GAT | TTG | AGC | AAT | GGT | GCA | GAT | 1161 |
| Ser | Asn | Gly | Thr | Arg | Leu | Ser | Ala | Ser | Asp | Leu | Ser | Asn | Gly | Ala | Asp | |
| | 355 | | | | | 360 | | | | | 365 | | | | | |
| GGG | ATG | CTG | GCC | ACG | AGC | TCC | AAT | GGG | TCT | CAG | TAC | AGC | GGC | TCC | AGG | 1209 |
| Gly | Met | Leu | Ala | Thr | Ser | Ser | Asn | Gly | Ser | Gln | Tyr | Ser | Gly | Ser | Arg | |
| 370 | | | | | 375 | | | | | 380 | | | | | 385 | |
| GTC | GAG | ACC | CCT | GTG | TCC | TAC | GTT | GGG | GAG | GAT | GAT | GAC | GAC | GAT | GAT | 1257 |
| Val | Glu | Thr | Pro | Val | Ser | Tyr | Val | Gly | Glu | Asp | Asp | Asp | Asp | Asp | Asp | |
| | | | | 390 | | | | | 395 | | | | | 400 | | |
| GAC | TTT | AAT | GAG | AAC | GAC | GAG | GAG | GAT | TGATTACTCA | ACCCGTAGAC | | | | | | 1304 |
| Asp | Phe | Asn | Glu | Asn | Asp | Glu | Glu | Asp | | | | | | | | |
| | | | 405 | | | | | 410 | | | | | | | | |

```
CCCTCTCCCC TTCGAATCAG CTTCAGGAAA AACACGTATA GAGGAAAGAA ACTTAAAGTG    1364

GGGCTTTCTG TTCTTTTTGG CCTACTCCCA AGAAGATACC CGCGAGTTCT GGAGTTGAGT    1424

GTGCAGCTCC AAGTGAGGAG GAGTGTGCGC AGTTTGAGCC TAGCTGCGGA TGTGTTGTGA    1484

AGCCAGCGTG CTAATGCAGA GCCTCTATCT ACCTTTTAGG ATTTTATGGT TTCTCTCTTT    1544

TCTCTCTTTT TTTTCCTTTT CTTTCTTTTT TGAGTTTGAA GCTTATTTTG CCCCTCAACA    1604

GTTGTTGCTG GGTTTGCCGA GGAAACTGTA CTGCGCCCAC ACCAGTGACA ATGACAAAGT    1664

GCTGCCCTGC CTCCGATGTC CAGCACCCAG GTGGTG                              1700
```

( 2 ) INFORMATION FOR SEQ ID NO: 2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Met | Ala | Lys | Asp | Ala | Ser | Leu | Ile | Glu | Ala | Asn | Gly | Glu | Leu | Lys | Val |
| 1 | | | | 5 | | | | | 10 | | | | | 15 | |
| Phe | Ile | Asp | Gln | Asn | Leu | Ser | Pro | Gly | Lys | Gly | Val | Val | Ser | Leu | Val |
| | | | 20 | | | | | 25 | | | | | 30 | | |

| | | | | | | | | | | | | | | |
|---|---|---|---|---|---|---|---|---|---|---|---|---|---|---|
| Ala | Val | His | Pro | Ser | Thr | Val | Asn | Thr | Leu | Gly | Lys | Gln | Leu | Pro |
| | | 35 | | | | 40 | | | | | 45 | | | |
| Lys | Thr | Phe | Gly | Gln | Ser | Asn | Val | Asn | Ile | Thr | Gln | Gln | Val | Val | Ile |
| | 50 | | | | | 55 | | | | | 60 | | | | |
| Gly | Thr | Pro | Gln | Arg | Pro | Ala | Ala | Ser | Asn | Thr | Ile | Val | Val | Gly | Ser |
| 65 | | | | | 70 | | | | | 75 | | | | | 80 |
| Pro | His | Thr | Pro | Asn | Thr | His | Phe | Val | Ser | Gln | Asn | Gln | Thr | Ser | Asp |
| | | | | 85 | | | | | 90 | | | | | 95 | |
| Ser | Ser | Pro | Trp | Ser | Ala | Gly | Lys | Arg | Asn | Arg | Lys | Gly | Glu | Lys | Asn |
| | | | 100 | | | | | 105 | | | | | 110 | | |
| Gly | Lys | Gly | Leu | Arg | His | Phe | Ser | Met | Lys | Val | Cys | Glu | Lys | Val | Gln |
| | | 115 | | | | | 120 | | | | | 125 | | | |
| Arg | Lys | Gly | Thr | Thr | Ser | Tyr | Asn | Glu | Val | Ala | Asp | Glu | Leu | Val | Ala |
| | 130 | | | | | 135 | | | | | 140 | | | | |
| Glu | Phe | Ser | Ala | Ala | Asp | Asn | His | Ile | Leu | Pro | Asn | Glu | Ser | Ala | Tyr |
| 145 | | | | | 150 | | | | | 155 | | | | | 160 |
| Asp | Gln | Lys | Asn | Ile | Arg | Arg | Arg | Val | Tyr | Asp | Ala | Leu | Asn | Val | Leu |
| | | | | 165 | | | | | 170 | | | | | 175 | |
| Met | Ala | Met | Asn | Ile | Ile | Ser | Lys | Glu | Lys | Lys | Glu | Ile | Lys | Trp | Ile |
| | | | 180 | | | | | 185 | | | | | 190 | | |
| Gly | Leu | Pro | Thr | Asn | Ser | Ala | Gln | Glu | Cys | Gln | Asn | Leu | Glu | Val | Glu |
| | | 195 | | | | | 200 | | | | | 205 | | | |
| Arg | Gln | Arg | Arg | Leu | Glu | Arg | Ile | Lys | Gln | Lys | Gln | Ser | Gln | Leu | Gln |
| | 210 | | | | | 215 | | | | | 220 | | | | |
| Glu | Leu | Ile | Leu | Gln | Gln | Ile | Ala | Phe | Lys | Asn | Leu | Val | Gln | Arg | Asn |
| 225 | | | | | 230 | | | | | 235 | | | | | 240 |
| Arg | Gln | Ala | Glu | Gln | Gln | Ala | Arg | Arg | Pro | Pro | Pro | Asn | Ser | Val |
| | | | | 245 | | | | | 250 | | | | | 255 |
| Ile | His | Leu | Pro | Phe | Ile | Ile | Val | Asn | Thr | Ser | Arg | Lys | Thr | Val | Ile |
| | | | 260 | | | | | 265 | | | | | 270 | | |
| Asp | Cys | Ser | Ile | Ser | Asn | Asp | Lys | Phe | Glu | Tyr | Leu | Phe | Asn | Phe | Asp |
| | | 275 | | | | | 280 | | | | | 285 | | | |
| Asn | Thr | Phe | Glu | Ile | His | Asp | Asp | Ile | Glu | Val | Leu | Lys | Arg | Met | Gly |
| | 290 | | | | | 295 | | | | | 300 | | | | |
| Met | Ala | Cys | Gly | Leu | Glu | Ser | Gly | Asn | Cys | Ser | Ala | Glu | Asp | Leu | Lys |
| 305 | | | | | 310 | | | | | 315 | | | | | 320 |
| Val | Ala | Arg | Ser | Leu | Val | Pro | Lys | Ala | Leu | Glu | Pro | Tyr | Val | Thr | Glu |
| | | | | 325 | | | | | 330 | | | | | 335 | |
| Met | Ala | Gln | Gly | Ser | Ile | Gly | Gly | Val | Phe | Val | Thr | Thr | Thr | Gly | Ser |
| | | | 340 | | | | | 345 | | | | | 350 | | |
| Thr | Ser | Asn | Gly | Thr | Arg | Leu | Ser | Ala | Ser | Asp | Leu | Ser | Asn | Gly | Ala |
| | | 355 | | | | | 360 | | | | | 365 | | | |
| Asp | Gly | Met | Leu | Ala | Thr | Ser | Ser | Asn | Gly | Ser | Gln | Tyr | Ser | Gly | Ser |
| | 370 | | | | | 375 | | | | | 380 | | | | |
| Arg | Val | Glu | Thr | Pro | Val | Ser | Tyr | Val | Gly | Glu | Asp | Asp | Asp | Asp | Asp |
| 385 | | | | | 390 | | | | | 395 | | | | | 400 |
| Asp | Asp | Phe | Asn | Glu | Asn | Asp | Glu | Glu | Asp |
| | | | | 405 | | | | | 410 |

( 2 ) INFORMATION FOR SEQ ID NO: 3:

( i ) SEQUENCE CHARACTERISTICS:
        ( A ) LENGTH: 16 amino acids
        ( B ) TYPE: amino acid
        ( D ) TOPOLOGY: linear (xi) SEQUENCE DESCRIPTION: SEQ ID NO: 3:

Arg Val Glu Thr Pro Val Ser Tyr Val Gly Glu Asp Asp Asp Asp Asp
1               5                   10                  15

ASSAY FOR INHIBITORS OF DP-1 AND OTHER DP PROTEINS

This invention is based on the transcription factor DP-1 and its role in controlling the cell cycle. It also relates to assays for DP-1, DP-2 and DP-3 inhibitors that interfere with cell growth, as well as for modulators of the phosphorylation state of the DP proteins.

The cellular transcription factor DRTF1/E2F integrates cell cycle events with the transcription apparatus through its cyclical interactions with important regulators of cellular proliferation. Two sequence specific DNA binding proteins, DP-1 and E2F-1, are components of DRTR1/E2F which synergistically interact in a DP-1/E2F-1 heterodimer. In this application it is shown that DP-1 is a very frequent, possibly universal, component of DRTF1/E2F in 3T3 cells since it is present in all forms of the DNA binding activity which occur during cell cycle progression. Furthermore, the DP-1 polypeptide, which is phosphorylated, undergoes a phosphorylation-dependent mobility shift during the cell cycle suggesting that its level of phosphorylation is regulated during cell cycle progression. This finding can be employed in assays to detect changes in the phosphorylation state of DP-1. A C-terminal region in DP-1 can interact with pRb which, in the context of the DP-1/E2F-1 heterodimer, contributes to the efficiency of pRb binding. The DP-1/E2F-1 heterodimer specifically interacts with the adenovirus type 5 E4 orf 6/7 protein, to produce a DNA binding activity which binds co-operatively to and transcriptionally activates through two appropriately positioned E2F sites in a manner which resembles the regulation of DRTF1/E2F by E4 orf 6/7 during adenovirus infection. One can also conclude that DP-1 is a frequent and cell cycle-regulated component of DRTF1/E2F, and that in the DP-1/E2F-1 heterodimer it is functionally important for recognition by pRb and the E4 orf 6/7 protein.

The molecular events that occur during the cell cycle need to be integrated with the transcription apparatus so that gene expression can be synchronised with cell cycle progression.

Control of the cell cycle is fundamental to the growth and maintenance of eukaryotic organisms, including mammalians and amphibians. Before a typical cell can divide (undergo mitosis), it must double its mass and duplicate all its contents. Most of the work involved in preparing for division goes on invisibly during the growth phase of the cell cycle, denoted as interphase. Interphase is divided into 3 periods. $G_1$ is used to denote the gap between the completion of the previous division and the start of DNA synthesis. The length of $G_1$ can be variable and cells can be held in a quiescent state of hours, days or longer. Cells in such a quiescent state are sometimes referred to as being in the $G_o$ phase.

Following $G_1$, cells enter the S phase during which DNA synthesis occurs. This is followed by a second gap, $G_2$, which is then followed by the M phase, i.e. mitosis. Generally, once cells enter the S phase they are committed to mitosis.

An important aspect of understanding and controlling the uncontrolled growth of cells is thus understanding the mechanisms by which cells undergo transition from $G_1$ to S phase.

Recently, a transcription factor called DRTF1 or E2F has been identified and shown to bind to pRb, the protein product of the retinoblastoma susceptibility gene, an anti-oncogene or tumour suppressor gene (see for example Wagner and Green, Nature 352, 189–190, 1991). It is widely believed that the cellular transcription factor DRTF1/E2F functions as a key component in cell cycle control because it associates with important cell cycle regulating proteins, such as the retinoblastoma gene product (pRb), p107, cyclins and cyclin-dependent kinases and furthermore its transcriptional activity is modulated by certain viral oncoproteins, such as adenovirus Ela, SV40 large T antigen, and the human papilloma virus E7 protein.

It is widely believed that the cellular transcription factor DRTF1/E2F plays a pivotal role in co-ordinating cell cycle progression through its interactions with important regulators of cellular proliferation, like the retinoblastoma tumour suppressor gene product (pRb), the pRb-related protein p107, cyclins and $p33^{cdk2}$ (Bandara and La Thangue, 1991; Bandara et al., 1991, 1992; Chellappan et al., 1991; Mudryj et al., 1991; Devoto et al., 1992). Furthermore, DRTF1/E2F DNA binding activity is regulated during cell cycle progression (Mudryj et al., 1991; Shirodkar et al., 1992; Schwartz et al., 1993) and differentiation (La Thangue and Rigby, 1987), processes which correlate with the transcriptional activity of some of the genes which contain E2F sites in their control sequences, for example dihydrofolate reductase, DNA polvmerase α and cdc2 (Means et al., 1992; Blake and Azizkhan, 1989; Dalton, 1992). Its activity is also regulated by certain viral oncoproteins, such as the adenovirus Ela protein, SV40 large T antigen and the human papilloma virus E7 protein, which sequester pRb and the other associated proteins from DRTF1/E2F, converting it from a transcriptionally inactive form to an active form (Hiebert et al., 1992; Zamanian and La Thangue, 1992, 1993). It is likely that the deregulation of DRTF1/E2F is important for the transforming and immortalizing functions of these oncoproteins (Bagchi et al., 1991; Bandara and La Thangue, 1991; Zamanian and La Thangue, 1992).

Another important feature of DRTR1/E2F concerns its regulation in adenovirus infected cells where its activity is modulated through a direct interaction with a viral protein (Huang and Hearing, 1989; Marton et al., 1990). Thus, in adenovirus infected cells, the binding of DRTF1/E2F to the adenovirus E2a promoter is much more stable than in uninfected cells because of the co-operative recognition of the two E2F sites in the E2a promoter (Hardy and Shenk, 1989; Raychaudhuri et al., 1990). This co-operativity requires the E2F binding sites to be correctly spaced and orientated, such as the arrangement which occurs in the E2a promoter (Hardy and Shenk, 1989). The viral protein responsible for this effect is the orf 6/7 protein, a product of the E4 region, which directly interacts with DRTF1/E2F in infected cells (Huang and Hearing, 1989; Marton et al., 1990). Since this interaction leads to co-operative recognition, it is likely that one function of the orf 6/7 protein is to sequester two DNA binding units of DRTF1/E2F into a complex, thus favouring the recognition of viral promoters over cellular promoters. However, the composition of the DRTF1/E2F DNA binding activity recognised by orf 617, and the significance of orf 6/7 induced co-operativity for transcriptional activity, has yet to be formally established.

Some progress has been made in identifying the proteins which comprise DRTF1/E2F. The first to be characterised, referred to as E2F-1, was isolated through its ability to directly bind to pRb (Helin et al., 1992; Kaelin et al., 1992; Shan et al., 1992). In contrast, DP-1 was defined as a component of DRTF1/E2F after biochemical purification of DRTF1 from F9 embryonal carcinoma (EC) cells (Girling et al., 1993).

DP-1 is also a component of HeLa cell DRTF1/E2F (Bandara et al., 1993) and occurs in both pRb and p107- associated DRTF1/E2F (Girling et al., 1993). Both E2F-1 and DP-1 proteins contain a small region of similarity (Girling et al., 1993) which allows them to interact with each other, to form a heterodimeric DNA binding activity which efficiently recognises and activates transcription through the E2F binding site in a synergistic fashion (Bandara et al., 1993; Helin et al., 1993). Although a DP-1/E2F-1 heterodimer is present in HeLa cells (Bandara et al., 1993), the distribution and regulation of the DP-1 protein is not known.

In the present invention, the characterisation of several important properties of the DP-1 is reported. In 3T3 cells DP-1 is a frequent, if not general, DNA binding component of DRTF1/E2F. Furthermore DP-1. which is phosphorylated, undergoes a phosphorylation-dependent mobility shift during cell cycle progression. The DP-1/E2F-1 heterodimer efficiently interacts with pRb and a domain in DP-1 is defined which can bind to pRb and which influences the interaction of pRb with heterodimer, possibly through direct binding. The adenovirus orf 6/7 protein binds to the DP-1/E2F-1 heterodimer, resulting in a DNA binding activity which has the biochemical and functional properties of the adenovirus infected cell form of DRTF1/E2F. DP-1 is thus a frequent component of DRTF1/E2F whose phosphorylation level during the cell cycle is regulated and which is functionally important for recognition by pRb and the orf 6/7 protein.

The sequence of the cDNA encoding DP-1 is presented here as Seq. ID No. 1. DP-1 is described further in International Patent Publication No. WO-A-94/10307, the contents of which are incorporated by reference.

The present invention is based in particular on the finding that DP-1 is phosphorylated during the cell cycle, and that DP-1 binds to DNA in the hypophosphorylated state. In other words, when DP-1 is phosphorylated, it does not have as great an affinity for DNA as it does when either not phosphorylated or hypophosphorylated. This can be extended to other DP proteins (eg. DP-2 and DP-3) whose activity also appears to be regulated by phosphorylation.

The present invention uses this finding to assay for agents which prevent or inhibit the hypophosphorylation, eg. of DP-1, or which enhance the phosphorylation of DP proteins such as DP-1. Such agents can be used to prevent or delay entry of the cell cycle into S phase from $G_1$. Antibodies against the regions of DP-1 which undergo a change in phosphorylation during the cell cycle may also be used in such assays, and to identify proliferating cells.

The present invention thus provides in a first aspect an assay for a potential growth prevention, inhibiting or enhancing agent, the assay comprising:

(i) bringing the agent into contact with a cell (eg. containing DP-1 or another DP protein); and (ii) observing the phosphorylation state of the DP protein.

The invention also extends to an agent obtainable from such an assay. The agent may be used in a method of controlling uncontrolled cell proliferation. Such a method may comprise administering to an individual with cells undergoing uncontrolled cell proliferation an effective amount of the agent.

In a simpler form, the assay of the invention in a second aspect comprises:

(i) providing a medium (eg. an extract from a cell) which contains a DP protein in a hypophosphorylated state;

(ii) bringing the medium into contact with the agent; and (iii) observing the phosphorylation state of the DP protein.

This assay can be used to screen agents which have the ability to activate the kinase which phosphorylates DP-1, thereby reducing its affinity for DNA.

The assay of the invention in a third aspect comprises:

(i) providing a medium (eg. an extract from a cell) which contains a DP protein in a phosphorylated state;

(ii) bringing the medium into contact with the agent; and (iii) observing the phosphorylation state of the DP protein.

A fourth aspect of the invention relates to an assay for a potential DP protein phosphorylation modulating agent, the assay comprising:

(i) contacting medium, which may be a cell, or an extract from a cell, which contains a DP protein in a hyphophosphorylated or phosphorylated state and a phosphorylating and/or dephosphorylating enzyme (eg. kinase or a phosphatase); and (ii) observing the phosphorylation state of the DP protein.

This assay may be used to screen agents which have the ability to maintain DP-1 in a phosphorylated state or alternatively prevent hypophosphorylation of DP-1.

Agents which may inhibit phosphorylation are likely to be kinase (a phosphorylator) antagonist or a phosphatase (a dephosphorylator) agonist while agents that activate, stimulate or encourage phosphorylation are likely to be kinase agonists or phosphatase antagonists. Agents contemplated here may include fragments, mutants and, homologues of kinases or phosphatases.

Source of kinases and phosphatases are recombinant proteins, purified proteins or biochemical fractions from cell extracts.

A "DP protein" as used herein refers not only to DP-1, although that is preferred, but also DP-2 and DP-3 and other related proteins of the same family having the same activity. Although DP-1 is the protein of choice the invention is not limited to DP-1 (unless the context requires otherwise).

The term "DP-1", with reference to assays, can comprise the amino acid sequence of Seq. ID. No. 2, homologues thereof, and fragments of the sequence and its homologues, which are capable of functioning as a mammalian transcription factor. In particular, the term "DP-1" may comprise:

(a) the protein of Seq. ID No. 2;

(b) an allelic variant or species homologue thereof;

(c) a protein at least 70% homologous to (a);

(d) a fragment of any one of (a) to (c) capable of forming a complex with the E2F-1, E2F-2, E2F-3, E2F4 or E2F-5; or (e) a fragment of any one of (a) to (c) of at least 15 amino acids.

These proteins may be in hypophosphorylated, partially or fully phosphorylated forms. Also included are labelled forms of such polypeptides (see page 8).

All polypeptides within this definition are referred to below as DP-1, unless the context specifically requires otherwise. The terms "DP-2" and "DP-3" should be construed likewise with of course part (a) being amended to refer to the amino acid sequences of DP-2 and DP-3, respectively.

An allelic variant will be a variant which will occur naturally in a murine animal and which will function to regulate gene expression in a substantially similar manner to the protein of the natural protein eg. of Seq. ID No. 2 for DP-1. Similarly, a species homologue will be the equivalent protein which occurs naturally in another species, including man, and which performs the equivalent function in that species to the DP protein (for DP-1 the sequence of Seq. ID No. 2) in murine animals. Within any one species, a homologue may exist as several allelic variants, and these will all be considered homologues of the (eg. Seq. ID No. 2 for DP-1) protein. Allelic variants and species homologues can be obtained by following the procedures described herein for the production of the polypeptide eg. of Seq. ID No. 2 for DP-1 and performing such procedures on a suitable cell source, e.g from a rodent carrying an allelic variant or another species. Since the polypeptide appears to be evolutionarily conserved it will also be possible to use, for example, a DP-1 nucleotide sequence to probe libraries made from rodent or other cells in order to obtain clones encoding the allelic or species variants. The clones can be manipulated by conventional techniques to identify a polypeptide of the invention which can then be produced by recombinant or synthetic techniques known per se. Preferred species homologues include mammalian or amphibian species homologues.

A-protein at least 70% homologous to the sequence (eg. Seq. ID No. 2) will be preferably at least 80 or 90% and more preferably at least 95% homologous to the protein (eg. of Seq. ID No. 2) over a region of at least 20, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology").

Generally, fragments of the DP protein (eg. Seq. ID No. 2 for DP-1) or its allelic variants or species homologues thereof capable of forming a complex with one of the E2F proteins E2F-1 to E2F-5 will be at least 10, preferably at least 15, for example at least 20, 25, 30, 40, 50 or 60 amino acids in length.

It will be possible to determine whether fragments form a complex with an E2F protein by providing the E2F protein and the fragment under conditions in which the E2F protein and the DP protein normally form a trans-activating transcription factor (if applicable), and determining whether or not a complex has formed. The determination may be made by, for example, measuring the ability of the complex to bind an E2F binding site in vitro, or alternatively, determining the molecular weight of the putative complex by methods such as SDS-PAGE.

Preferred fragments include those which are capable of forming a trans-activation complex with E2F-1 or its related family members. For example, the fragment can be added to E2F-1 in the presence of a reporter gene construct adapted to be activated by the DP protein/E2F-1 complex. Such an experiment will determine whether the fragment has the necessary activity.

The DP protein may be labelled with a revealing label. The revealing label may be any suitable label which allows the polypeptide to be detected. Suitable labels include radioisotopes, eg. $^{125}$I, enzymes, antibodies and linkers such as biotin.

The DP protein (optionally labelled) may also be fixed to a solid phase, for example the wall of an immunoassay dish. The cell extract may then be added to the dish or other solid phase environment in the presence of the agent to determine whether hypophosphorylation or phosphorylation is inhibited or enhanced.

In the first aspect of the invention, the cell with which the agent is brought into contact may be any cell in which the DP protein expressed. This includes mammalian (including human, primate and rodent) cells and amphibian cells (including *Xenopus* cells).

The cell may a cell which is maintained in in vitro culture. In conducting the assay, the cell may be maintained in a quiescent state (eg. in $G_0$). This can be achieved by growing cells in a serum free medium. Techniques for achieving this are well known in the art and suitable media are commercially available. This will be desirable in that the assay may be conducted on a population of cells which are maintained in synchronous culture so that the effects of the agent in affecting the phosphorylation state of the DP protein at any particular point in the cell cycle may be determined. The cell may be a primary cell, a transformed cell or a tumour cell.

The DP protein may be the native protein of the cell or may be expressed by a recombinant DNA construct within the cell. The expression may be transient from an extrachromosomal element or from a stably integrated recombinant DNA in the cell. The constructs may comprise a DNA encoding a DP protein operably linked to a promoter compatible with the host cell. Such constructs may be made using conventional recombinant DNA techniques such as those disclosed in Sambrook et al (Molecular Cloning: A Laboratory Manual, 1989).

In all aspects of the invention, the phosphorylation state of a DP protein may be measured by any suitable technique available to those of skill in the art.

For example, the mobility of a DP protein on a SDS/polyacrylamide gel is dependent on its state of phosphorylation. DP-1 has an apparent molecular weight on such gels of about 55,000. However it appears in two forms, termed "p55U" (upper) and "p55L" (lower). The forms differ in their degree of phophorylation the p55U having a higher level than p55L. In other cell types, the 55 kd protein may appear in other forms which are also due to phosphorylation differences. Thus electrophoresis of an extract from the cells which are undergoing an assay according to the invention followed by immunoblotting may be used to determine the relative amounts of p55L and p55U in a sample and thus the phosphorylation state of DP-1.

The DP protein (eg. DP-1) may also be assayed by growing cells prior to the assay in a medium which contains a labelled phosphate group which may become attached to DP-1 via the natural processes in the cell. The amount of labelled DP-1 in the presence or absence of the agent can then be measured, for example by immunoprecipitating DP-1 using an anti-DP-1 antibody and then measuring the amount of label precipitated. DP-1 antibodies may be obtained by reference to WO-A-94/10307.

Another method of assaying DP protein is to measure its ability to form a complex with E2F-1 (or another member of the E2F family) and, optionally, to determine the ability of the complex to activate transcription. This may be done by reference to the techniques described in WO-A-94110307.

In a one embodiment of the invention, the candidate agent may be assayed using a fragment of a DP protein (reference to a fragment includes synthetic or recombinant peptides corresponding to such a fragment) which has been phosphorylated. In this embodiment a cell, or an extract thereof, can be brought into contact with the agent in the presence of the phosphorylated fragment and the amount of dephosphorylation of the fragment which occurs measured.

The fragment of eg. DP-1 is preferably derived from the C-terminal region of DP-1. For example, it may comprise a fragment of from 20 to 50 amino acids (eg. 25, 30 or 40 amino acids) derived from a contiguous sequence within the final 100 (eg. 90, 80, 60, 50, 40 or 30) amino acids of the sequence SEQ ID No. 2. A preferred fragment is from amino acids 385 to 400 of this sequence, and peptides which comprise (or bracket) this region, e.g 375–410, 375405, 375400, 380410, 380405, 380400 are also desirable.

It has been found that a monoclonal antibody raised (anti-DP-1 (D)) against a synthetic peptide (D) corresponding to residues 385400 of Seq. ID No. 2 recognizes DP-1 in its hypophosphorylated state (since the synthetic peptide is unphosphorylated) but binds less well to DP-1 when phosphorylated. This indicates that hypophosphorylation of DP-1 occurs at least in part in this region of the protein.

Thus in an assay using a DP-1 fragment the fragment may be phosphorylated at a suitable phosphorylation site, for example $^{388}$Thr or $^{391}$Ser. Phosphorylation may be carried out enzymatically, using a suitable kinase enzyme or chemically. Techniques for phosphorylation are known in the art.

The DP protein or fragment thereof may be phosphorylated with a labelled, eg. radiolabelled, phosphate group. The amount of dephosphorylation which occurs in the presence of the agent can then be measured by any suitable technique. For example, the DP protein may be recovered from the mixture of the cell or extract by affinity chromatography or size separation on a suitable matrix, eg. a gel or HPLC column, and the amount of labelled DP protein measured. The amount of DP-1 still labelled can be compared to a control in which no agent is used. The amount of free labelled phosphate in the medium could also be measured. An agent active in preventing the hypophosphorylation of the DP protein will reduce the amount of free phosphate released from the DP-1 protein.

The label may take the form of a protein (eg. GST) fused to the DP protein (to form a fusion protein) to assist in the purification and/or detection of DP.

The phosphorylation status of DP-1, DP-2 or DP-3 may also be measured by the use of an antibody which recognises the unphosphorylated, but not phosphorylated, form. As previously mentioned an antibody has been raised against a synthetic peptide corresponding to residues 385–400 of Seq. ID No. 2 (referred to later as peptide D SEQ ID No:3) that recognizes DP-1 in its hypophosphorylated state. Such an antibody may be made using standard techniques for the production of hybridomas, and used in an assay of the invention by first of all adding the labelled DP-1 and candidate agent to the cell or extract thereof, incubating the mixture obtained (typically for anywhere between 0.5 to 60, eg. 1–30 or 5–15 minutes at between 10–40, eg. about 20°, 25°, 30° or 37° C.) and then adding the antibody to the mixture to determine the amount of dephosphorylation of the DP-1 which has occured. The antibody should be added in molar excess to the starting amount of DP-1 in order to bind all unlabelled DP-1 which has been produced.

Alternatively, the antibody may be used in an analogous manner to determine the amount of phosphorylation when the DP protein is assayed in the presence of an extract containing an activity in which the kinase which phosphorylates a DP protein is present.

The amount of agent which may be used in the assay may vary over a wide range, depending upon factors such as its potential level of activity, toxicity or solubility. Typical concentrations of the agent when brought into contact with a cell or extract thereof will be from about 1 nM to 100 mM, e.g from 10 nM to 10 mM.

Where the assay is performed using a fragment of a DP protein, the amount of fragment will be in the range of from about 1 nM to 100 mM, e.g from 10 mM to 10 mM.

Suitable candidate agents include peptide fragments of DP-1 (whether produced by synthetic or recombinant means), including C-terminal fragments. Such fragments include those C-terminal fragments mentioned above. Agents which have activity in the assay can be refined and developed to produce higher activity agents by methods such as molecular modelling or peptide scanning.

Other agents include those that can affect or influence the activity of enzymes that can alter the DP protein phosphorylation state. Enzymes contemplated include kinases (which phosphorylate) and phosphatases (which dephosphorylate). Thus candidate agents may be agonists or antagonists of kinases and/or phosphatases and may be able to modulate DP protein phosphorylation.

The extract of cells for use in the invention are suitably extracts from the types of cells mentioned above, preferably obtained from cells in synchronous culture, and thus is in a defined stage of the cell cycle, eg. $G_1$ or S. This includes cells transformed or transfected with a recombinant DNA encoding the DP protein. The extracts may be obtained from cells which have been labelled with radioactive phosphate and the phosphorylation status of DP-1 may be measured in the manner described for the first aspect of the invention. Methods for preparing suitable extracts of cellular proteins are well known in the art.

In a fifth aspect the invention provides a monoclonal antibody obtainable by using a peptide corresponding to the C-terminal region of Seq. ID No. 2 as an immunogen, which antibody recognizes the DP protein in its hypophosphorylated state but binds less well to the DP protein when phosphorylated. This indicates that hypophosphorylation of DP-1 occurs at least in part in this region of the protein. Thus antibodies contemplated are ones that can bind to hypophosphorylated DP (i.e. without phosphate groups) but not to the phosphorylated form.

The C-terminal region of DP-1 is preferably a fragment of from 20 to 50 amino acids (eg. 25, 30 or 40 amino acids) derived from a contiguous sequence within the final 100 (eg. 90, 80, 60, 50, 40 or 30 amino acids) of the sequence ID No. 2. A preferred fragment is from amino acids 385 to 400 of this sequence, and peptides which bracket or include this region, e.g 375410, 375405, 375400, 380410, 380–405, 380–400 are also preferred. If the sequence 385 to 400 is used as an immunogen (peptide D SEQ ID No: 3) one obtains the monoclonal antibody anti-DP-1 (D) whose preparation is described later.

The fifth aspect also extends to antibodies specific for, or raised using, :an immunogen containing a phosphorylation site, and such antibodies may thus be capable of binding to a portion of a DP protein which comprises a phosphorylation site. In particular the sequence 385400 of DP-1 is mentioned here as it contains the phosphorylation sites Thr$^{398}$ and Ser319 (see FIG. 9).

The monoclonal antibody may be derived from any suitable mammalian source, eg. murine or rat. For the purposes of this invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, eg. as described in EP-A-0239400.

The antibody may be produced by conventional hybridoma techniques or, in the case of modified antibodies or fragments, by recombinant DNA technology, e.g by the expression in a suitable host vector of a DNA construct encoding the modified antibody or fragment thereof operably linked to a promoter. Suitable host cells include bacterial (eg. E. coli), yeast, insect and mammalian cells.

Where the assay of the invention involves the use of a vector introduced into a cell encoding a DP protein, the nucleotide sequence encoding DP may include a contiguous sequence of nucleotides Which is capable of selectively hybridizing to eg. Seq. ID. No 1 or to the complement of Seq. ID No. 1. The nucleotide sequence may comprise DNA or RNA.

A nucleotide sequence capable of selectively hybridizing to the DNA of Seq. ID No. 1 will be generally at least 70%, preferably at least 80 or 90% and more preferably at least 95% homologous to the DNA of Seq. ID No 1 over a region of at least 20, preferably at least 30, for instance at least 40, 60 or 100 or more contiguous nucleotides.

The nucleotide sequence may also include a sequence coding for the protein of Seq. ED No. 2 or a fragment thereof.

A nucleotide sequence such as a DNA nucleotide sequence may be produced recombinantly, synthetically, or by any means available to those of skill in the art. It may be also cloned by reference to the techniques disclosed in WO-A-94/10307.

Agents which have been identified as either stimulating phosphorylation of a DP protein or inhibiting the development of hypophosphorylation may be provided as pharmaceutical formulations. Such formulations comprise the agent together with a pharmaceutically acceptable carrier or diluent.

Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Agents identified in accordance with the invention, and the above-mentioned compositions thereof may be used for the treatment, regulation or diagnosis of conditions, including proliferative diseases, in a mammal including man. Such conditions include those associated with abnormal (e.g at an unusually high or low level) and/or aberrant (e.g due to a mutation in the gene sequence) expression of one or more transcription factors such as the E2F factor (cloned by Helin et al) or the protein of Seq. ID No. 2 or the E2F-1 protein or related family members. The conditions also include those which are brought about by abnormal expression of a gene whose gene product is regulated by the protein of Seq. ID No. 2. Treatment or regulation of conditions with the above-mentioned agents and compositions will usually involve administering to a recipient in need of such treatment an effective amount of a polypeptide, antibody, fragment thereof or composition.

One group of preferred agents are polypeptides based upon the region of amino acids 160–220 of Seq. ID No. 2. This region of the protein has a homology of about 40% to a similar region of the E2F-1 protein described by Helin et al (ibid) and both regions are putative alpha-helical regions. While not wishing to be bound by any one particular theory, it is thought that the heterodimerisation of E2F and DP-1 is mediated through these homologous regions.

A sixth aspect of the invention relates to a fragment of a DP protein which comprises a phosphorylation site (which may be phosphorylated, or not phosphorylated, as desired), Suitable sites include $Thr^{388}$ and $Sep^{191}$ found in DP-1. Preferred fragments have already been mentioned (see pages 12 and 13).

Figure 1B:
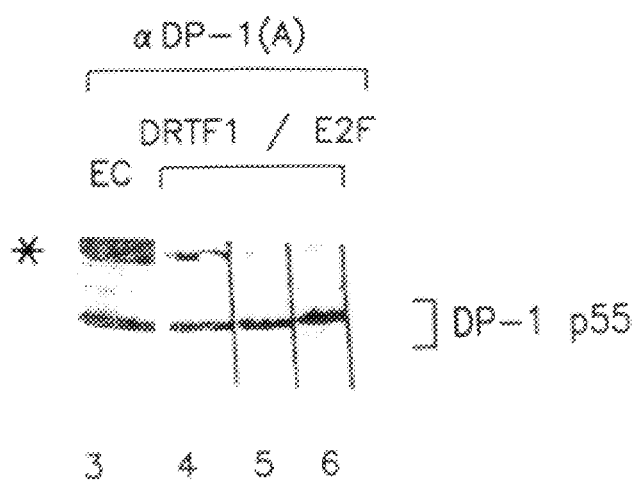

The invention will now be described, by way of example, with reference to the following Examples and accompanying drawings which are provided to illustrate the invention, and should not be construed as being limiting. In the drawings:

FIG. 1 shows the characterisation of DP-1.

Anti-DP-1 (A) was assayed for reactivity with an F9 EC cell extract (tracks 1 and 2) in the presence of either the homologous peptide A (track 1) or the control peptide 1 by immunoblotting. p55 is indicated; p55U is the predominant polypeptide although p55L is just visible. * indicates p65 (see text). The presence of p55 in different fractions which contain purified DRTF1/E2F DNA binding activity is shown in tracks 4, 5 and 6 (for comparison p55 and p65 in an F9 EC cell extract is shown in track 3); DRTF1/E2F DNA binding activity was purified as described previously (Girling et al., 1993). Note that the presence of p55 correlates with DRTF1/E2F DNA binding activity.

FIG. 2 shows the cell cycle-regulation of DP-1 in 3T3 cells.

a) DP-1 is a frequent DNA binding component of DRTF1/E2F during cell cycle progression:

3T3 cells were serum starved and then stimulated to progress through the cell cycle. Cultures were harvested every 4 h, extracted, and assayed (about 8 µg) for DRTF1/E2F DNA binding activities (tracks 2 to 17). In parallel cultures, progression into S phase was assayed using the incorporation of BrdU which indicated that the majority of cycling cells entered S phase between 8 and 12 h. The presence of DP-1 in the DRTF1/E2F DNA binding complexes was tested by assessing the effect of anti-DP-1 (A) (tracks 2 to 17) in the presence of a control (peptide 1; tracks 10 to 17) or the homologous (peptide A; tracks 2 to 9) peptide.

Anti-DP-1 reacted with most of the detectable DRTF1/E2F DNA binding complexes.

b) Cyclin A in DRTF1/E2F during the 3T3 cell cycle:

The synchronised 3T3 cell extracts assayed in a) were assessed for the presence of cyclin A in DRTF1/E2F using a rabbit polyclonal anti-cyclin A (lower panel) which was compared to the preimmune control serum (upper panel). The effect of this anti cyclin A was to cause a faster migrating DRTF1a (the slowest migrating) complex. For example the slower migrating DRTF1a which occurred between 0 and 4 h (indicated by the D) was not apparent in the presence of anti-cyclin A (compare tracks 1, 2 and 3 in upper and lower panels).

c) p107 in DRTF1/E2F during the 3T3 cell cycle:

The synchronised 3T3 cell extracts were assessed for the presence of p107 in DRTF1/E2F using a p107 monoclonal antibody supernatant (lower panel) which was compared to the effect of an unrelated control monoclonal antibody supernatent (upper panel). The anti-p107 shift is indicated by the arrow (>).

d) DP-1 is a cell cycle-regulated DNA binding component of DRTF1/E2F:

The synchronised 3T3 cell extracts were immunoblotted with anti-DP-1 (A). Approximately 40 µg of each microextract were assayed. Note that two forms of DP-1 p55 were resolved, referred to as p55U (upper) and p55L (lower). p55L became apparent between 8 and 12 h post-serum stimulation, and thus correlated with the induction of DRTF1b/c, the transcriptionally active form of DRTF1/E2F (tracks 4 and 5 in (a)). The cross-reacting p65 polypeptide is indicated by *.

e) Regulation of DP-1 during the differentiation of F9 EC cells.

Anti-DP-1 (A) was assayed for reactivity with extracts prepared from F9 EC (track 1) or differentiated F9 PE (7 days post-induction of differentiation; track 2) cells by immunoblotting. Note that the two forms of p55 (U and L) are detectable, both of which are down-regulated during the differentiation process. The cross-reacting polypeptide (*) remains unchanged.

FIG. 3 shows DP-1 is a phosphorylated protein.

a) Characterisation of anti-DP-1 (D): anti-DP-1 (D) was assessed for its effects on DRTF1/E2F DNA binding activity (tracks 2 and 3) in the presence of the homologous peptide, D (track 2) or the unrelated peptide, 1 (track 3). Note that anti-DP-1 (D) reacted with DRTF1/E2F (tracks 3). The reactivity of anti-DP-1 (D) with a GST-DP-1 fusion protein was assessed in the presence of the unrelated peptide, 1 (track 4) or homologous peptide, D (track 5).

b) immunoprecipitation with anti-DP-1: immunoprecipitation from $^{32}$p orthophosphate metabolically radiolabelled cell lysates was performed with anti-DP-1 (A) (tracks 1 and 2) in the presence of the homologous peptide, A (track 1) or unrelated peptide. 1 (track 2). Polypeptides were released from the immunoprecipitate performed in the presence of peptide 1 (track 2) and re-immunoprecipitated with anti-DP-1 (D) (tracks 3 and 4) in the presence of either the homologous peptide, D (track 3) or unrelated peptide, 1 (track 4). DP-1 (p55) and p70 are indicated. In parallel, DRTF1/E2F DNA binding activity was assessed in the first immunoprecipitation with anti-DP-1 (A) (tracks 5 and 6) and after re-immunoprecipitation with anti-DP-1 (D) (tracks 7 and 8) in the presence of the indicated competing peptides. The polypeptides resolved in the second immunoprecipitation with anti-DP-1 (D) in the presence of unrelated peptide 1 or peptide D (tracks 10 and 9 respectively) were compared to those defined by immunoblotting with an F9 EC cell extract with anti-DP-1 (A) (track 11). The size of the immunoprecipitated p70 is considerably larger than the cross-reacting polypeptide defined with anti-DP-1 (A) (compare track 10 with 11; cross-reacting polypeptide indicated by ●). Standard molecular weights are shown in track 12. Note that tracks 1, 2, 3 and 4 are derived from exposing a single polyacrylamide gel (tracks 1 and 2 being a shorter exposure) and that tracks 9, 10, 11 and 12 are derived from the same polyacrylamide gel.

c) Phosphatase treatment of 3T3 cell extracts: immunoblotting was performed with anti-DP-1(A) with 3T3 cell extracts that had been treated with (track 2) or without (track 1) phosphatases (see page 33). In the control treatment (track 2), both p55U and p55L are resolved, together with a non-specific polypeptide (*). After treating with phosphatase (track 1), p55L becomes less apparent.

FIG. 4 shows the interaction of DP-1 with pRb.

a) Either wild-type (WI) DP-1 (about long; tracks 3 and 9) or various mutant DP-1 proteins (about long; tracks 4 to 7 and 10 to 13) were assessed as a heterodimer with EF-1 (about 5 ng) for E2F site DNA binding activity and ability to interact with wild-type GST-pRb$^{379-928}$ (about 5 ng; tracks 2 to 7) or GST-A22 (about 5ng; tracks 8 to 13); the Rb-DP-1/E2F-1 complex is indicated. The activity of E2F-1 alone is shown in tracks 2 and 8, and the probe alone in track 1. Note that the interaction of GST-pRb with the DP-1Δ211/E2F-1 heterodimer was compromised relative to the wild-type DP-1/E2F-1 complex. The numbering of the DP-1 proteins indicates the position of the C-terminal residue; Δ73–340 lacks protein sequence from the N- and C-terminal regions.

b) The indicated proteins, DP-1 (tracks 1 to 5 and 12), E2F-1 (tracks 6 to 8), E1a (tracks 9 to 11 and 13 to 15) and CREBP1 (tracks 16 to 19) were transcribed and translated in vitro and assessed for binding activity to either GST protein (tracks 2 and 19), GST-pRb (tracks 3, 6, 9, 13 and 18), GST-C→F (706) (tracks 4, 7, 10, 14 and 17), GST-Δ22 (tracks 5, 8, 11, 15, and 16), GST-E2F-1 (track 12) or the Sepharose beads alone (track 1). In vitro translated CREBP1 is shown in track 20, and tracks 13, 14 and 15 show reduced exposure 20 of tracks 10, 11 and 12.

c) The indicated DP-1 proteins (WT, Δ341, Δ327, Δ73–340 and Δ211 were in vitro transcribed and translated and assessed for binding activity to either GST-pRb (tracks 1 to 5) or GST protein alone (tracks 6 to 10). The in vitro translated Δ211 polypeptide used in this experiment is shown in track 11. Note that the ability of Δ211 to interact with GST-pRb is compromised. In b) and c), about 2 μg of GST or GST-fusion protein was mixed with reticulocyte lysate containing the translated polypeptide. All the polypeptides were translated with approximately equivalent efficiency. The panels shown in (c) were derived from the same experiment and the autoradiographs exposed for the same length of time.

Figure 5:
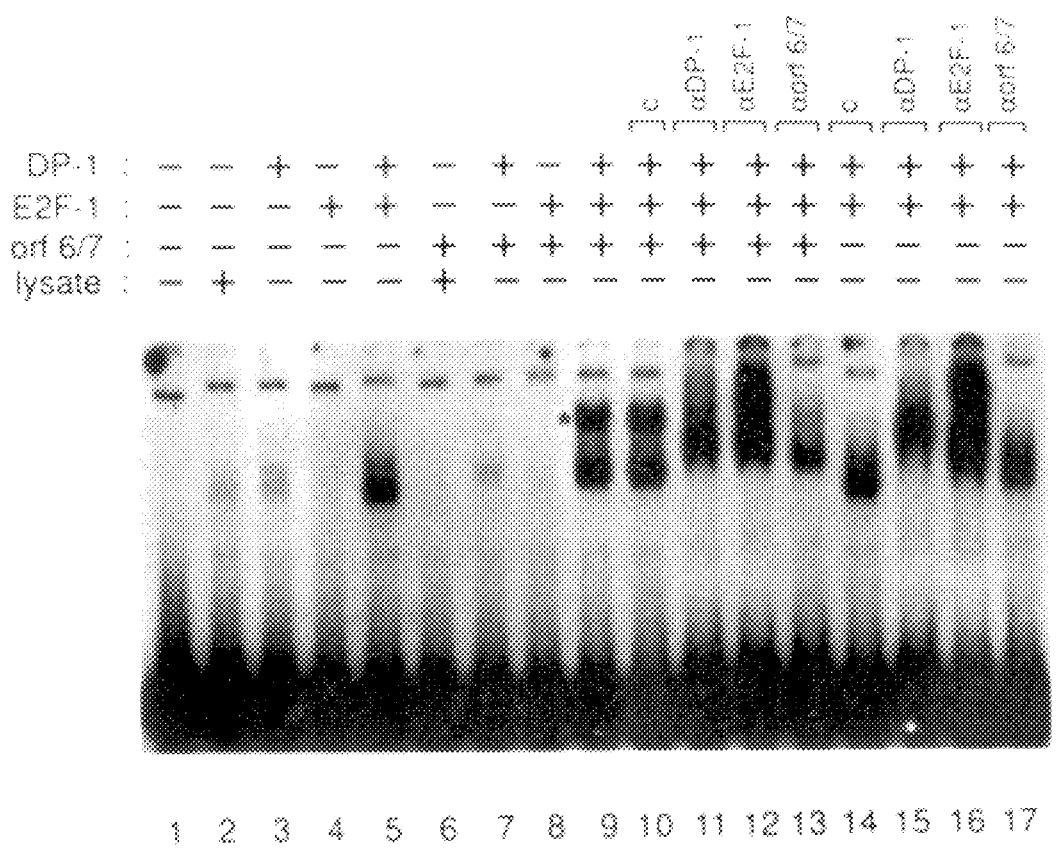

FIG. 5 shows the adenovirus type 5 orf 6/7 protein binds to the DP-1/E2F-1 heterodimer.

The DNA binding activity of in vitro translated DP-1 or E2F-1 proteins was assessed alone (tracks 3 and 7 for DP-1, and tracks 4 and 8 for E2F-1) or together (tracks 5 and 9 to 17) in the presence of purified orf 617 fusion protein (tracks 6 to 13); the activity of the lysate alone was assessed in tracks 2 and 6. Anti-DP-1 (tracks 11 and 15), anti-E2F-1 (tracks 12 and 16), anti-orf 6/7 protein (tracks 13 and 17) or a control antibody (c; tracks 10 and 14) were included in the binding reaction to establish the presence of each protein in the DP-1/E2F-1 heterodimer. DP-1 and E2F-1 were provided after in vitro translation in rabbit reticulocytes extracts and the assay was performed on the adenovirus E2a promoter (−96 to +68). The orf 6/7 double site complex is indicated in track 9 by the *.

Figure 6A:
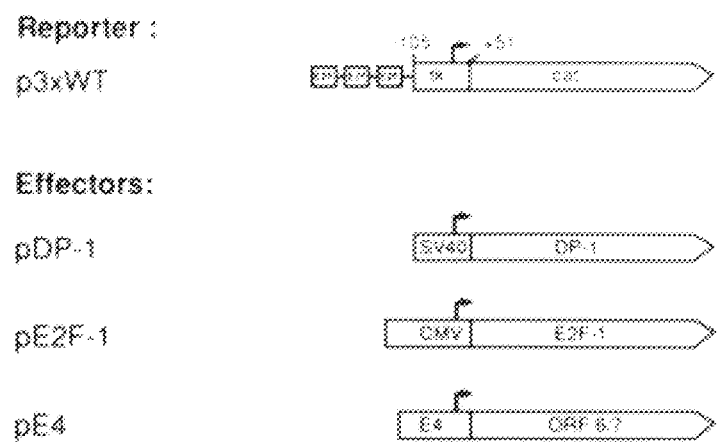

FIG. 6 shows the orf 6/7 protein regulates transcription driven by the DP-1/E2F-1 heterodimer in a promoter-dependent fashion.

a) Summary of constructs: pDP-1, pE2F-1 and pE4 orf 6/7 express full length proteins, and p3xWT contains three E2F sites in tandem (Zamanian and La Thangue, 1992). The arrows indicate the arrangement of the E2F sites.

b) *Drosophila melanogaster* SL2 cells were transfected with p3xWT and the indicated expression vectors. As previously observed, DP-1 and E2F-1 interact synergistically in E2F site dependent transcriptional activation (track 7); the presence of the orf 6/7 protein failed to significantly affect transcriptional activity (track 8).

FIG. 7 shows the orf 6/7 protein activates transcription driven by the DP-1/E2F-1 heterodimer in the context of the adenovirus E2a promoter.

a) Summary of constructs: pDP-1, pE2F-1 and pE4 orf 6/7 express full length proteins, and pE2a contains the Ad5 wildtype E2a promoter sequence (−96 to +68). The arrows indicate the arrangement of the E2F sites.

b) and c) *Drosophila melanogaster* SL2 cells were transfected with pE2a and the indicated expression vectors. The presence of the orf 6/7 protein together with the DP-1/E2F-1 heterodimer enhanced the activity of DE2a (compare lanes 7 and 8). All values are expressed relative to pE2a alone which was given an arbitrary value of 1.0, and are representative of at least three separate experiments.

Figure 8:
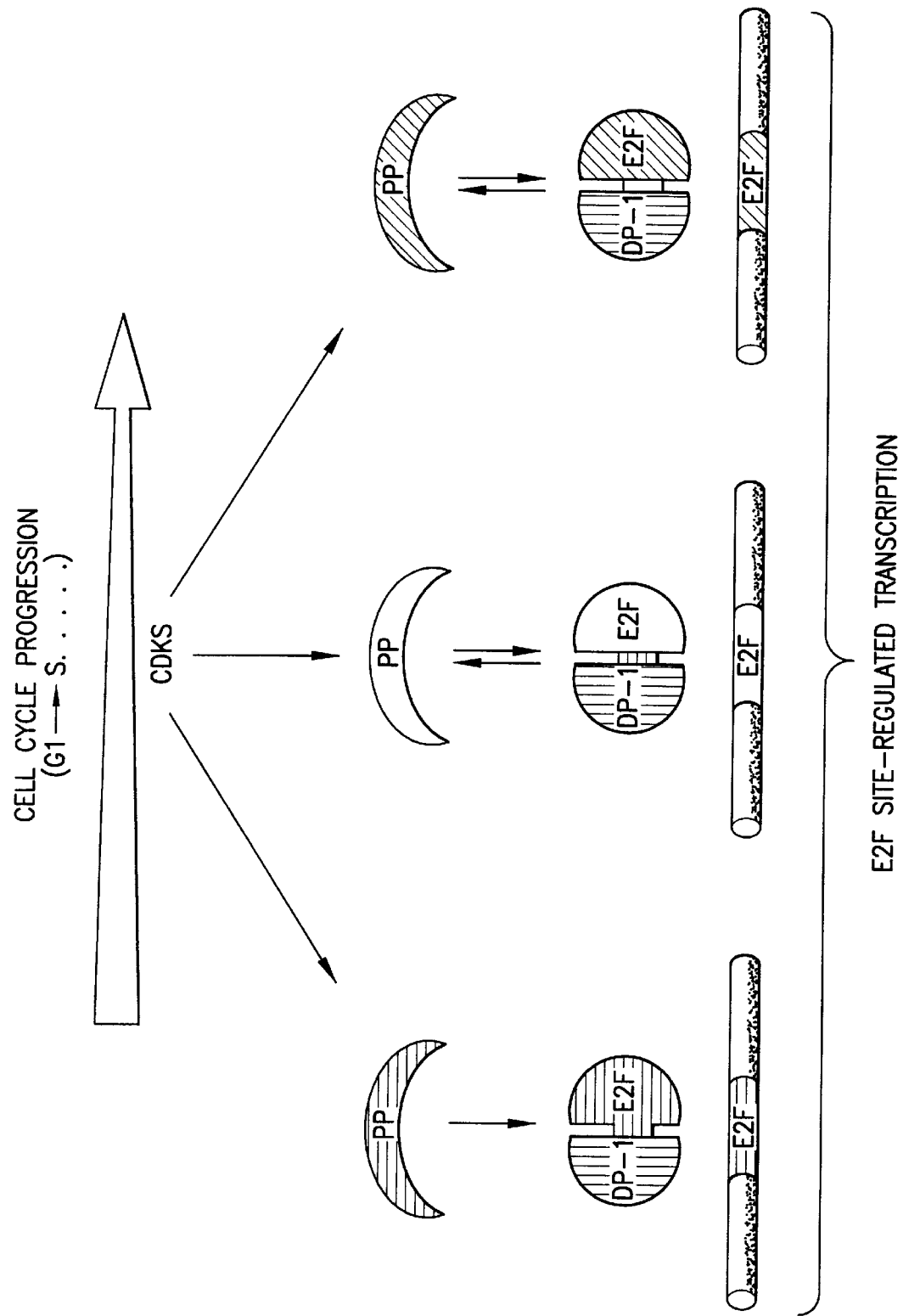

FIG. 8 shows a model depicting the composition and regulation of DRTF1/E2F during cell cycle progression in 3T3 cells.

It is suggested that during cell cycle progression proteins, such as pRb and p107 (indicated by pp in the diagram), bind to and regulate the activity of distinct DP-1/E2F heterodimers (where E2F could be E2F-1 or another protein which can heterodimerize with DP-1, indicated by the different shading), the nature of the pp being dictated by the E2F component. Based on the results presented in this study, DP-1 could also be modified during cell cycle progression.

Figure 9:
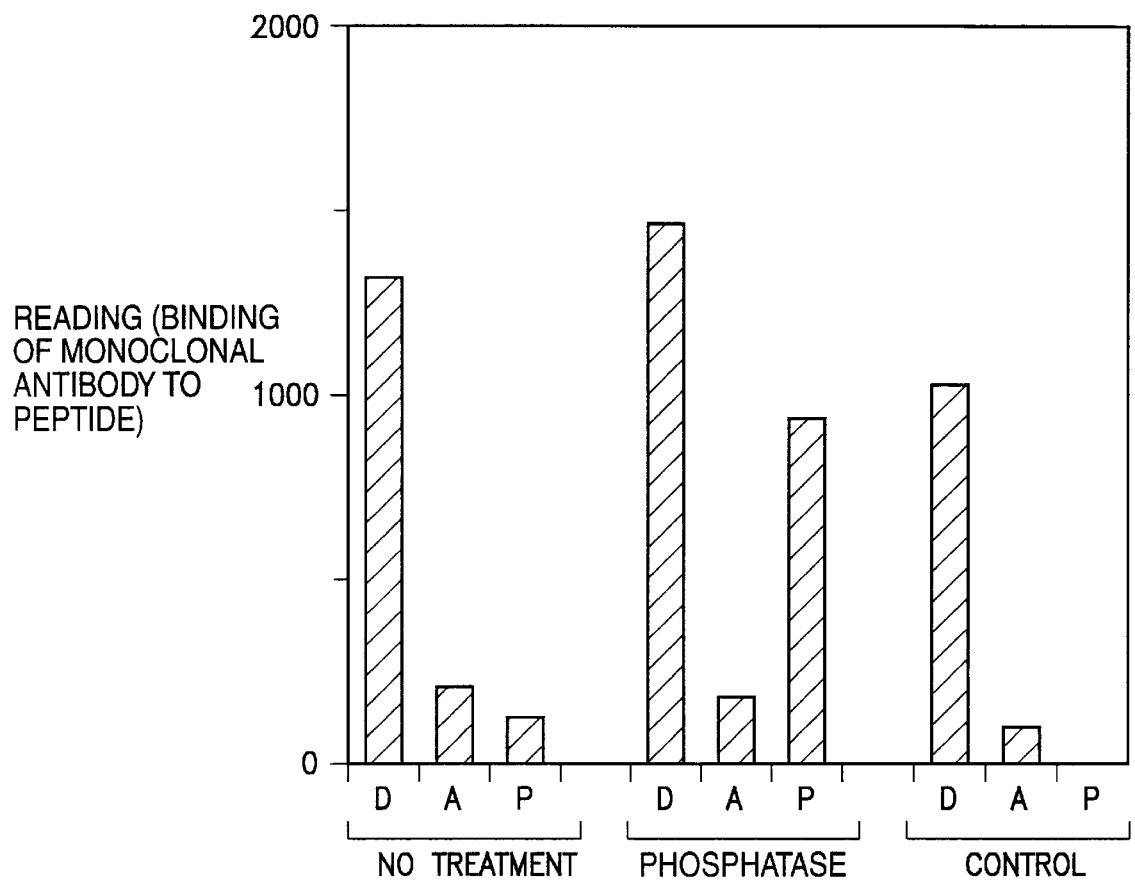

FIG. 9 is a bar graph showing the results of an ELISA assay where a monoclonal antibody recognises hypophospharylated peptide D (SEQ ID No: 3). The mAb binds to the hypophosphorylated, but not the phosphorylated, form of DP-1.

EXAMPLES

Immunochemical characterisation of immunochemical characterisation of DP-1.

DP-1 is a DNA binding component of DRTF1/E2F in F9 EC and HeLa cell extracts, a conclusion which rests on the fact that the E2F site-specific DNA binding complexes resolved in these extracts react with anti-DP-1 antibodies (Bandara et al., 1993; Girling et al., 1993). It was decided to determine whether changes in DRTF1/E2F DNA binding activity were reflected in the properties of the DP-1 protein and thus chose to characterise DP-1 in two situations where DRTF1/E2F DNA binding activity is regulated, that is, during the differentiation of F9 EC cells (La Thangue and Rigby, 1987) and cell cycle progression (Mudryj et al., 1991; Shirodkar et al., 1992).

For this, an anti-DP-1 serum was used raised against an N-terminal peptide anti-DP-1 (A), which was purified by peptide affinity chromatography and used to probe cell extracts. Two distinct polypeptides were revealed in F9 EC cell extracts with molecular weights of 65,000 and 55,000 (referred to as p65 and p55 respectively), both being specifically recognised by anti-DP-1 because they were absent when the homologous, but not an unrelated peptide, was included in the antibody reaction (FIG. 1, compare track 1 and 2). In F9 EC cell extracts, p55 resolved as a closely migrating doublet Qust visible in FIG. 1, track 2), a feature which was particularly clear in extracts prepared from other types of cells, such as 3T3 cells (discussed later); these two forms of p55 will subsequently be referred to as p55U and p55L. In F9 EC cell extracts, p55U usually was much more abundant then p55L.

It is thought that p55 is the product of the DP-1 gene since it is recognised by several anti-DP-1 antisera raised against peptides derived from other regions of the DP-1 protein (for example, see FIG. 3b) whereas p65 has been defined only with anti-peptide A. suggesting that p65 is a cross-reacting polypeptide. The results presented here which demonstrate that p55 correlates with DRTF1/E2F DNA binding activity is consistent with this idea, as is the fact that the predominant polypeptide derived from translating DP-1 MnRNA in vitro has approximately 55,000 molecular weight (see FIG. 4b). Furthermore, when anti-DP-1 was used to probe chromatography fractions derived from the affinity purification of DRTF1/E2F DNA binding activity, p55, rather than p65, correlated with E2F site DNA binding activity (FIG. 1, tracks 3, 4, 5 and 6). p55 is thus likely to be the DP-1 protein.

DP-1 is cell cycle and differentiation regulated.

The system which was chosen to explore the cell cycle regulation of DP-1 was progression through the cell cycle after stimulation of serum starved 3T3 cells. In this cell system, DRTF1/E2F DNA binding activity undergoes a series of cell cycle-dependent changes. For example, DRTF1a(complexed DRTF1/E2F) was the predominant species of DNA binding activity in serum starved (GO) cells (FIG. 2a, track 2). However, after serum stimulation and once progression through the cell cycle was underway, the DNA binding activity of DRTF1b//c (the transcriptionally active form of DRTF1/E2F) increased towards the end of G1, to reach a maximum level in S phase (12h post stimulation; FIG. 2a, track 5). Chances in the mobility of the DRTF1a complex also occurred during cell cycle progression. For example, between 0 and 4 h post stimulation a slower migrating form of DRTF1a became apparent (FIG. 2a, compare tracks 2 and 3). This persisted throughout the remainder of the cycle, its appearance correlating with the presence of cyclin A in DRTF1a since the addition of anti-cyclin A to the binding reaction prevented the appearance this slower migrating complex (FIG. 2b, compare the mobility of DRTF1a between tracks 1 and 2 for upper and lower panels; indicated by arrow). On the other hand, DRTF1a complexes which contain the Rb-related protein p107 were present throughout cell cycle progression, including GO extracts, since anti-p107 caused the appearance of a slower migrating complex at all time points (FIG. 2c; compare upper and lower panels; shifted complex indicated by arrow). The cell cycle regulation and composition of DRTF1/E2F observed here is in general agreement with studies performed by others (Mudryj et al., 1991; Shirodkar et al., 1992; Schwartz et al., 1993).

Although previous studies had suggested that DP-1 is a frequent component of DRTF1/E2F, these experiments were performed in extracts prepared from a synchronous cultures of cells (Girling et al., 1993; Bandara et al., 1993) and one can not exclude the possibility that the presence of DP-1 in DRTF1/E2F was nevertheless cell cycle-regulated. To determine if DP-1 is present in DRTF1/E2F during a discrete phase of the cell cycle the effect of anti-DP-1 in the extracts of synchronised 3T3 cells was assessed. Anti-DP-1 affected most of the DRTF1/E2F DNA binding complexes which occur during the 3T3 cell cycle (FIG. 2a, tracks 10 to 17). These effects were specific since they were competed by the homologous peptide (peptide A) but not an unrelated peptide (peptide 1; FIG. 2a, compare tracks 2 to 9 with 10 to 17). DP-1 is thus a frequent, and based on these results possibly common, component of 3T3 cell DRTF1/E2F.

The results suggest that DP-1 is a frequent component of DRTF1/E2F, although it is possible that the DP-1 protein is modified during cell cycle progression. This possibility was investigated by immunoblotting the same set of synchronized 3T3 cell extracts. In serum starved 3T3 extracts p55U was resolved although upon cell cycle progression p55L appeared 20 towards the end of G1, as the cells were entering S phase FIG. 2d, compare tracks 2, 3 and 4), and thus the appearance of p55L correlated well with the increased DRTF1/E2F DNA binding activity apparent at this stage of the cell cycle (FIG. 2a, track 5). It was concluded that DP-1 is a frequent component of DRTF1/E2F during the 3T3 cell cycle and that it is likely to be modified during cell cycle progression. In the next section the data presented suggests that the appearance of p55L results from changes in the level of phosphorylation.

DRTF1/E2F DNA binding activity is down-regulated during the process of F9 EC cell differentiation (La Thangue and Rigby, 1987; Partridge and La Thangue, 1991), a regulatory profile which correlates with a decrease in the rate of proliferation. When extracts prepared from differentiating F9 cells in which DRTF1/E2F DNA binding activity was down-regulated were used for immunoblotting, it was apparent that the decreased DNA binding activity in differentiated cells (7 days post induction of differentiation) correlated with a reduced level of both p55U and p55L (FIG. 2e, compare tracks 1 and 2), a profile which contrasts with the regulation of p55 during cell cycle progression (FIG. 2d). It was therefore concluded that cell cycle progression and differentiation affect DP-1 in distinct ways.

DP-1 is a phosphorylated protein.

Figure 3A:
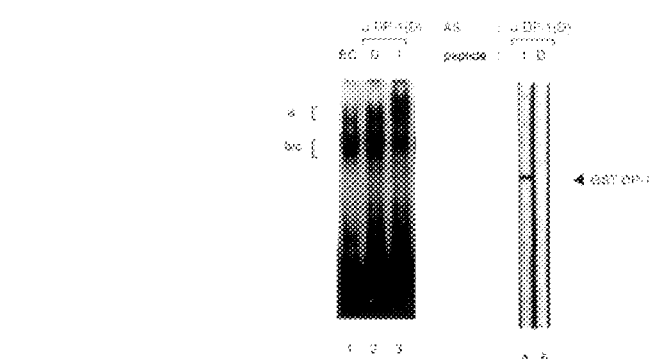

A possible explanation for the modulation of DP-1 p55 during cell cycle progression was that it reflected post-translational modification of p55, one possibility being its level of phosphorylation. Whether DP-1 is phosphorylated was tested. To investigate this possibility, two different anti-DP-1 peptide antisera were used. As described earlier, anti-DP-1(A) recognises a peptide sequence in the N-terminal region of DP-1, whereas anti-DP-1(D) was raised against a peptide sequence located in the extreme C-terminal region of DP-1 (see Materials and Methods). Anti-DP-1(D) specifically reacted with DRTF1/E2F DNA binding activity in gel retardation conditions (FIG. 3a, compare tracks 2 and 3) and with a GST-DP-1 fusion protein (FIG. 3a, compare tracks 4 and 5).

The strategy adopted to test if DP-1 is phosphorylated was firstly to immunoprecipitate with anti-DP-1 (A) from extracts prepared from cells metabolically radiolabelled with $^{32}$p orthophosphate. Immunoprecipitated proteins were released from the anti-DP-1(A) complex by competing with peptide A, that is, the peptide used to prepare the antiserum and re-immunoprecipitated with anti-DP-1 (D). Polypeptides resolved after the second immunoprecipitation should be either DP-1, or DP-1-associated proteins.

Figure 3B:
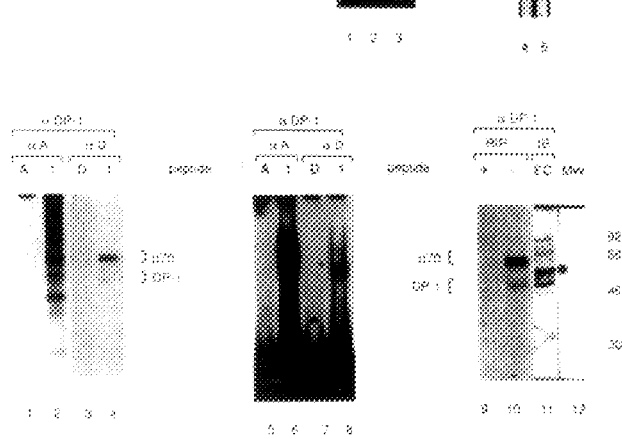

In the first immunoprecipitation several polypeptides were specifically immunoprecipitated with anti-DP-1 (A) (FIG. 3b, compare tracks 1 and 2). Re-immunoprecipitation of the released polypeptides with anti-DP-1 (D) revealed a simpler pattern, resolving predominantly two phosphorylated polypeptides, with 55,000 and 70,000 molecular weights (FIG. 3b, compare tracks 3 and 4). Comparison of the immunoprecipitated polypeptides to those defined by immunoblotting with anti-DP-1(A) indicated that the 55,000 molecular weight polypeptide co-migrated with DP-1 p55 (FIG. 3b, compare tracks 10 and 11) and thus it is very likely to be DP-1. At this level of analysis, it was not possible to distinguish between p55U and p55L. Since the 70,000 molecular weight polypeptide (referred to as p70 in FIG. 3b, track 4) was present in the immunoprecipitations performed with both anti-DP-1 sera, it is probably physically associated with DP-1. It is important to note that the size of p70 was considerably larger than cross-reacting polypeptide p65 discussed earlier (indicated as ● in FIG. 3b, track 11). Both anti-DP-1(A) and anti-DP-1(D) immunoprecipitated DRTF1/E2F DNA binding activity (FIG. 3b, tracks 5 to 8), suggesting that this form of DP-1, probably in complex with p70, is involved in binding to the E2F site.

One can conclude that DP- 1 is phosphorylated and that it physically associates with at least one other phosphorylated polypeptide. Relative to p70, DP-1 had a low level of phosphorylation, a result consistent with the idea that DP-1 binds to DNA in the hypophosphorylated state.

Figure 3C:
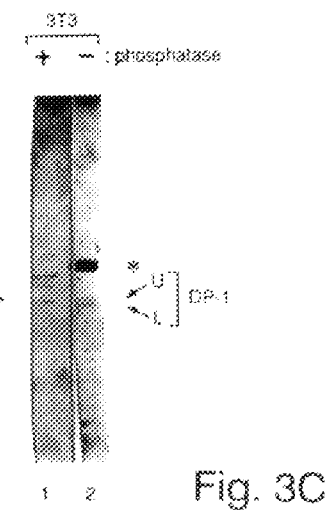

To test whether the mobility difference between p55U and p55L was influenced by phosphorylation, the effect of treating extracts prepared from a synchronous cultures of 3T3 cells with phosphatases was assessed. In the absence of phosphatase, both p55U and p55L could be resolved (FIG. 3c, track 2). However, after phosphatasing the extract, p55U became more apparent at the expense of p55L (FIG. 3c, compare tracks 1 to 2; p55U and p55L are indicated), suggesting that the difference between p55U and p55L is influenced by phosphorylation.

Increased binding of pRb to the DP-1/E2F-1 heterodimer.

The cell cycle studies presented here combined with previous studies suggest that DP-1 is a frequent component of DRTF1/E2F (Bandara et al., 1993; Girling et al. 1993). DRTF1/E2F is, however, most likely to be a heterodimeric DNA binding activity (Girling et al., 1993; Bandara et al., 1993; Helin et al., 1993). A potential physiological partner is the E2F-1 protein, since a DP-1/E2F-1 heterodimer has been detected in vivo and both proteins synergistically interact in vitro to form a heterodimeric DNA binding complex (Bandara et al., 1993; Helin et al., 1993). As a variety of proteins can interact with DRTF1/E2F, such as pRb, p107, cyclins A and E, and p33$^{cdk2}$ (Mudryj et al., 1991; Shirodkar et al., 1992; Lees et al., 1992; Schwartz et al., 1993), it was interesting to understand how DP-1 in the context of the DP-1/E2F-1 heterodimer influences these interactions. It was decided to explore the binding of pRb to the DP-1/E2F-1 heterodimer.

The efficiency with which wild-type pRb (as a GST fusion protein containing pRb sequence from residue 379 to 928) bound to the DP-1/E2F-1 heterodimer was assessed and compared to the binding activity with E2F-1 alone. Consistent with previous reports (Bandara et al., 1993; Helin et al., 1993) E2F-1 had low DNA binding activity when assayed alone (FIG. 4a, track 8). However, this activity was significantly greater when the same amount of E2F-1 was assayed in the presence of DP-1 (FIG. 4a, compare tracks 8 and 9). The addition of GST-pRb to the DP-1/E2F-1 heterodimer resulted in a slower migrating DNA binding complex (FIG. 4a, compare track 3 to 9). GST-pRb also bound to the E2F-1 complex although the intensity of the pRb-E2F-1 complex was less than with the DP-1/E2F-1 heterodimer (FIG. 4a, compare tracks 2 and 3), an effect in part due to the low DNA binding activity of E2F-1 alone.

It was possible that the enhanced binding of pRb to the DP-1/E2F-1 heterodimer is aided by an interaction between DP-1 and pRb which, in addition to the previously documented recognition of E2F-1 by pRb (Helin et al., 1992; Kaelin et al., 1992; Shan et al., 1992), helps stablise the binding of pRb to the heterodimer. This idea was tested using a binding assay where the interaction between in vitro translated DP-1 with GST-pRb was assessed, and which has previously been employed to study the interaction of DP-1 and E2F-1 (Bandara et al., 1993).

As a control for the specificity of this assay, the interaction of E2F-1 and E1a with pRb was assessed, both of which are known o bind to pRb in a fashion which is dependent on the integrity of the pocket (Hu et al., 1990; Helin et al., 1992; Kaelin et al., 1992). We compared their binding to both wild-type pRb and two pRb proteins encoded by naturally occurring mutant alleles which contain either a single amino acid substitution (C to F at residue 706) or lack the region of the protein encoded by exon 22. Both E2F-1 and E1a bound to pRb in a pocket-dependent fashion since their interaction with wild-type pRb was greater than with the mutant proteins (FIG. 4b, compare tracks 6 with 7 and 8, and 9 with 10 and 11, and reduced exposure in tracks 13, 14 and 15). Furthermore, and consistent with previous results (Bandara et al., 1993), DP-1 and E2F-1 it was possible to specifically bind to each other (FIG. 4b, compare tracks 1, 2 and 12). When the interaction of DP-1 with wild-type pRb was assessed a significant level of binding activity was detected (FIG. 4b, compare tracks 2 and 3). However, this activity was not dependent on the integrity of the pocket region of pRb since DP-1 bound with equal efficiency to both wild-type and the mutant pRb proteins (FIG. 4b, compare tracks 3, 4 and 5), although it was dependent on the presence of pRb protein sequence since there was reduced binding to either GST protein or the glutathione beads (FIG. 4b, compare track 1,2 and 3). One can conclude that DP-1 can specifically interact with pRb albeit in a pocket-independent fashion.

Two approaches were taken to control the specificity of the pRb-DP-1 interaction. Firstly, the interaction of an unrelated protein was assessed with pRb. For this, we chose CREBP1 (a cAMP response element binding protein; Maekawa et al., 1989) which in the conditions of this assay did not interact with either wild-type pRb or the mutant Rb proteins any more efficiently than with the GST protein (FIG. 4b, compare tracks 16,17,18 to 19). Secondly, the binding activity of a panel of mutant DP-1 proteins (FIG. 4c) was assessed with either wild-type pRb or GST alone. Almost all the DP-1 mutants assayed bound more efficiently to pRb than to GST alone (FIG. 4c, compare tracks 1, 2, 3 and 4 with 6, 7, 8 and 9). However, mutant Δ211, which lacks DP-1 protein sequence C-terminal from residue 211, failed to interact with pRb (FIG. 4c, compare tracks 5 to 10; the translated Δ211 polypeptide used in this assay is shown in track 11).

These mutant DP-1 proteins were also assessed for their ability to interact with E2F-1 and pRb in the gel retardation assay (FIG. 4a). All the mutant DP-1 proteins could synergistically interact with E2F-1 in E2F site DNA binding activity (FIG. 4a, tracks 9 to 13). The activity of Δ211 was marginally lower than wild-type DP-1 (FIG. 4a, compare tracks 9 to 13), consistent with earlier studies indicating that the region in DP-1 between residue 204 and 249 contributes to the DNA binding activity of the DP-1/E2F-1 heterodimer (Bandara et al., 1993).

As pointed out earlier, the DP-1/E2F-1 heterodimer efficiently interacts with pRb (FIG. 4a, track 3). The mutant DP-1 proteins which could interact with pRb in the binding assay (FIG. 4c) were also able to produce DP-1/E2F-1 heterodimers capable of interacting with pRb (FIG. 4a, compare track 3, 4, 5 and 6). The DP-1/E2F-1 heterodimer produced with Δ211. which failed to interact with pRb in the binding assay (FIG. 4c, track 5), had reduced pRb binding activity (FIG. 4a, compare tracks 3 and 7). The marginally reduced DNA binding activity of the Δ211/E2F-1 heterodimer was far less than the dramatic reduction in binding efficiency of pRb to the DP-1 A11/E2F-1 heterodimer (FIG. 4a, compare tracks 6 to 7 and 12 to 13). These data derived from studies on mutant DP-1 proteins in two different assays suggest that DP-1 can interact with pRb and that the region between residue 211 and 327 influences this interaction. The adenovirus E4 orf 6/7 protein binds to the DP-1/E2F-1 heterodimer and confers on the DNA binding complex the property of co-operative E2F site DNA binding.

It was decided to determine if the adenovirus orf 6/7 product can bind to the DP-1/E2F-1 heterodimer. This interaction was studied because the orf 6/7 protein interacts with two molecules of DRTF1/E2F DNA binding activity during adenovirus infection (Huang and Hearing, 1989; Marton et al., 1990), which leads to the co-operative recognition of two correctly spaced and orientated E2F binding sites, such as those which occur in the E2a promoter (Hardy and Shenk, 1989; Raychaudhuri et al., 1990), and thus an interaction between orf 6/7 and the DP-1/E2F-1 heterodimer would represent another example of an important physiological interaction.

In order to test this, DP-1 and E2F-1 proteins were translated in vitro and their DNA binding activity on the E2a promoter studied by gel retardation. Again, only in the presence of both proteins was significant DNA binding activity observed (FIG. 5, compare tracks 2, 3, 4 to 5). The addition of orf 6/7 protein to the DP-1/E2F-1 heterodimer caused a slower migrating DNA binding complex to appear (FIG. 5, indicated by * in track 9) which was not apparent when orf 6/7 was added to DP-1 or E2F-1 alone (FIG. 5, compare tracks 6, 7 and 8 to 9). This effect was specific for the arrangement of the two E2F binding sites in the E2a promoter since the orf 6/7 induced shift was not apparent when a single E2F binding site was used (data not shown). It is very likely therefore to represent a DNA binding complex which recognises the configuration of the E2F sites in the E2a promoter. These results indicate that the orf 6/7 protein interacts specifically with the DP-1/E2F-1 heterodimer and, in so doing, creates a DNA binding activity with the appropriate biochemical properties of the adenovirus infected cell form of DRTF1/E2F. The interaction of orf 6/7 with the DP-1/E2F-1 heterodimer therefore recapitulates the in vivo phenomenon.

The presence of DP-1, E2F-1 and the orf 6/7 protein in the double site complex was established using antisera which specifically recognise each protein. Anti-DP-1 and anti-E2F-1 reacted with the DP-1/E2F-1 heterodimer either in the absence or presence of the orf 6/7 protein (FIG. 5, compare tracks 10, 11 and 12, and 14, 15 and 16). In contrast, anti-orf 6/7 did not affect the activity of the DP-1/E2F-1 heterodimer (FIG. 5, compare tracks 13 to 17) but prevented the appearance of the double site complex which was apparent upon the addition of the orf 6/7 protein (FIG. 5, compare tracks 10 to 13). One can conclude therefore that DP-1, E2F-1 and the orf 6/7 protein are present in the double site complex.

A DP-1/E2F-1 heterodimer combined with an appropriate configuration of E2F sites are necessary for activation of E2F site dependent transcription by orf 6/7.

Figure 6B:
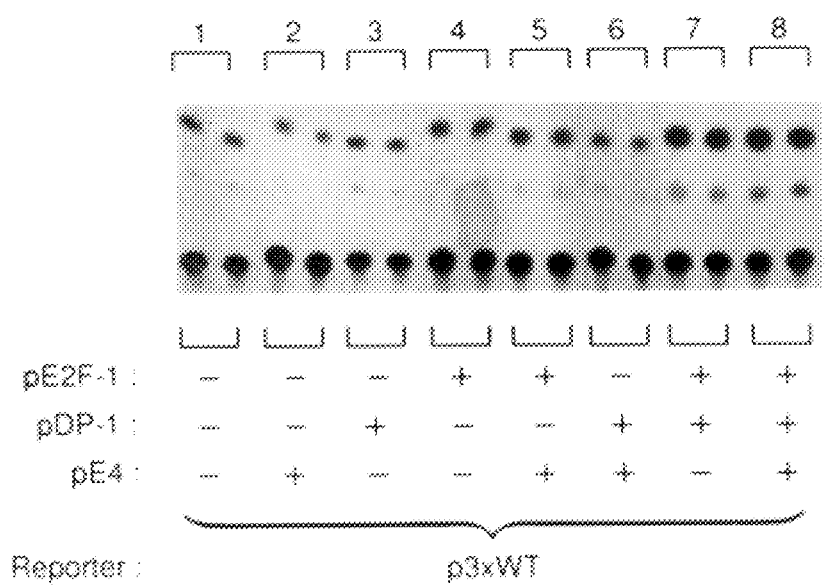

In order to establish the functional consequences of the interaction between the DP-1/E2F-1 heterodimer and orf 6/7, an assay system which was used has been previously developed in *Drosophila melanogaster* SL2 cells (Bandara et al., 1993). ST2 cells are particularly suitable for the analysis of E2F site-dependent transcription because they contain very low levels of endozenous E2F site DNA binding activity (Bandara et al., 1993), in contrast to many mammalian cells, and thus enable the activity of transfected E2F-site effector molecules expressed from Transfected vectors to be easily assessed. It has been previously shown that in these cells DP-1 and E2F-1 synergistically interact in E2F site-dependent transcriptional activation (when assayed by the p3xWT reporter), in conditions where each protein alone activates poorly (Bandara et al., 1993; and FIG. 6b, compare lanes 3 and 4 to 7). Co-expression of orf 6/7 with either DP-1 or E2F-1 alone, or in the presence of both proteins, failed to significantly affect the transcriptional activity of p3xWT (FIG. 6b, compare lanes 3 with 6, 4 with 5, and 7 with 8). This was the expected result based on the arrangement of the E2F sites in p3xWT, since it contains three copies in tandem of the distal E2F site from the adenovirus E2a promoter, and is therefore an inappropriate arrangement for formation of the orf 6/7-dependent double site complex (Hardy and Shenk, 1989).

When a similar assay was performed on the wild-type adenovirus E2a promoter, which contains an organisation of E2F sites (indicated by arrows in FIG. 7) which allows the formation of the orf 6/7-double site complex in adenovirus infected cells (Hardy and Shenk, 1989; and see FIG. 5), DP-1 and E2F-1 activated transcription more efficiently together than either protein alone (FIG. 7b and c, compare lane 7 to 3 and 4). However, co-expressing orf 6/7 together with DP-1 and E2F-1 produced a marked increase in the transcriptional activity of the E2a promoter (FIG. 7b and c, compare lanes 7 and 8) in contrast to the effect of orf 6/7 on p3xWT (FIG. 6b, compare lanes 7 and 8). This effect was specific for the DP-1/E2F-1 heterodimer because orf 6/7 did not affect promoter activity when either DP-1 or E2F-1 were expressed alone (FIG. 7b and c, compare track 3 to 6 and 4 to 5). Transcriptional activation by orf 6/7 is therefore dependent on the presence of DP-1 and E2F-1 proteins and, furthermore, requires an organization of E2F sites which has previously been shown to be necessary for the orf 6/7 protein to exert its biological effects in infected cells. The interaction of orf 6/7 with the DP-1/E2F-1 heterodimer therefore recapitulates the regulation of E2F site-dependent transcription in adenovirus infected cells.

DP-1: a frequent and proliferation-regulated DNA binding component of DRTF1/E2F.

DP-1 was initially defined as an E2F site DNA binding polypeptide in F9 EC cells and a component of pRb and p107 associated DRTF1/E2F (Girling et al., 1993). Furthermore, in extracts prepared from a synchronous cultures of F9 EC and HeLa cells, anti-DP-1 antibodies affect most of the definable DNA binding complexes (Bandara et al., 1993). In the present invention analysis of the DP-1 protein has continued by investigating its properties during the 3T3 cell cycle where DRTF1/E2F undergoes a regulated series of interactions with proteins, such as pRb and p107 (referred to as 'pocket' proteins), cyclins and cyclin-dependent kinases (reviewed in Nevins, 1992; La Thangue, 1994). The results clearly establish that during cell cycle progression in 3T3 cells, DP-1 is a very frequent, if not universal. DNA binding component of DRTF1/E2F. This contrasts with the results of studies performed on the E2F-1 protein which suggest that E2F-1 is a somewhat rarer DNA binding component since it is present in some, but not all, species of DRTF1/E2F (Chittenden et al., 1993). It is possible therefore that DP-1 can form heterodimers with other proteins during the cell cycle, which are perhaps related to E2F-1, producing other species of heterodimeric E2F site DNA binding activities (indicated in the model shown in FIG. 8). Based on the available evidence, it seems likely that a multiplicity of DNA binding heterodimers exist which recognise the E2F binding site and that certain cells (for example, F9 EC, HeLa and 3T3) have DP-1 as a frequent component with its partner, exemplified in this study by E2F-1, being variable. The isolation of proteins which are related to E2F-1 (Ivey-Hoyle et al., 1993; Lees et al., 1993), particularly within the DNA binding domain and which are therefore likely partners for DP-1, is consistent with such a model.

Although DP-1 is a frequent DNA binding component of DRTF1/E2F throughout the 3T3 cell cycle, the DP-1 DNA binding polypeptide (p55) nevertheless is subject to cell cycle modification because it underwent a slight mobility shift during cell cycle progression (from p55U to p55L). A possible explanation for this phenomenon is that the phosphorylation level of p55 is regulated during cell cycle progression, an idea consistent with the effect of phosphatase which altered the mobility of p55L (FIG. 3c). This suggests that the product of DP-1, p55, which is a frequent component of DRTF1/E2F in certain types of cells, is differentially phosphorylated during cell cycle progression. The functional consequences, the location of the residues, and the nature of the kinases and phosphatases involved in this process, are yet to be determined.

It is noteworthy that DP-1 physically associates with another phospho-protein, p70. Relative to DP-1, p70 possessed a greater level of phosphorylation, an observation consistent with the idea that DP-1 and p70 respond to different physiological cues. The presence of p70 in DP-1 immunoprecipitates correlated with DRTF1/E2F DNA binding activity and thus it is possible the DP-1, p70 complex is a heterodimeric E2F site-specific DNA binding complex. However, p70 does not appear to be E2F-1 since various anti-E2F-1 antisera have failed to react with it. This does not exclude that it is related to E2F-1 and it could, for example, be one of the more recently defined E2F-1 related proteins (Ivey-Hoyle et al., 1993; Lees et al., 1993).

In contrast to the regulation of DP-1 during cell cycle progression, DP-1 is down-regulated during the process of differentiation and thus in this respect its level correlates with the rate of cellular proliferation. Indeed, it is possible that the level of DP-1 directly influences the rate of cellular proliferation since many of the genes which contain E2F binding sites in their promoter regions encode proteins necessary for cell cycle progression (Nevins, 1992).

DP-1 binds to pRb.

The results show that DP-1 can bind to pRb in a fashion which is not dependent on the integrity of the pocket. This contrasts with the interaction of E2F-1 and viral oncoproteins with pRb because their binding activity is more efficient when the pocket region is intact.

A protein domain defined in the C-terminal half of DP-1 influences the binding efficiency of pRb to either DP-1 alone or the DP-1/E2F-1 heterodimer, suggesting that this domain is involved with mediating the increased binding of pRb. However, it is not wished to imply that this domain is believed to be sufficient for the interaction, but rather that it is likely to co-operate with the pocket-dependent interaction which occurs between pRb and the C-terminal domain in E2F-1 (Helin et al., 1993). pRb L2 failed to efficiently bind to the DP-1/E2F-1 heterodimer in the gel retardation assay although it was able to do so in the binding assay (FIG. 4a and b) suggesting that the interaction between DP-1 and pRb is weak. Alternatively, it is possible that E2F-1 may interfere with the ability of DP-1 to interact with Δ22 in the context of the DP-1/E° F-1 heterodimer. Further experiments will clarify these issues.

It is suggested therefore that E2F-1 is the principal determinant in influencing the binding of pRb to the DP-1/E2F-1 heterodimer but that this binding activity is enhanced through an interaction between a non-pocket-dependent region of pRb and a C-terminal region of DP-1. Given that DP-1 is also present in p107-DRTF1/E2F complexes, it is possible that DP-1 also aids the binding of p107 to the heterodimer. If this is the case then it may be a generic property of pocket proteins to recognise DP-1. It will be very interesting to test these ideas and determine the domain in pRb which binds to DP-1.

The interaction of the orf 6/7 protein with the DP-1/E2F-1 heterodimer recapitulates physiological regulation.

The results also suggest that the DP-1/E2F-1 heterodimer is a physiologically relevant form of DRTF1/E2F recognised by the orf 6/7 protein. Formation of the heterodimer and an appropriate arrangement of E2F sites (for example in the E2a promoter) is a pre-requisite for transcriptional activation by orf 6/7 indicating that the DP-1/E2F-1 heterodimer possesses the important hallmarks of the infected cell form of DRTF1/E2F. It is well documented that the orf 6/7 protein forms a stable complex with DRTF1/E2F DNA binding activities during adenovirus infection of HeLa cells (Hardy and Shenk, 1989; Huang and Hearing, 1989). Given that a DP-1/E2F-1 heterodimer exists in HeLa cells (Bandara et al., 1993), it is very likely that the orf 617 protein interacts with this complex during normal lytic infection. It is believed, therefore, that one has defined the components of and reconstructed the physiological interactions which occur during adenovirus infection with one form of DRTF1/E2F. However, it is likely that other DP-1/E2F heterodimers can also interact with orf 6/7, for example, DP-1/E2F-2 and DP-1/E2F-3, given the high degree of similarity between E2F-1, −2, and −3 (Ivey-Hoyle et al., 1993; Lees et al., 1993). In addition, other DP proteins, which are as highly related to DP-1 as E2F-1 is to E2F-2 and E2F-3 (Girling, Ormondroyd and La Thangue, unpublished observations), are likely partners for E2F1 (for example E2F-1).

Although the contribution of the orf 617 protein to creating a double E2F site DNA binding complex is relatively clear, little is known about its role in transcriptional activation. The data suggest that the orf 6/7 protein provides little, if any, transcriptional stimulation. This view is based on the fact that the orf 617 protein enhances the transcriptional activity of the DP-1/E2F-1 heterodimer about 2-fold (FIG. 7). The simplest interpretation therefore is that the orf 6/7 proteins favours the occupation of two sites (rather than one site which is likely to occur in the absence of orf 6/7), and that the enhanced transcriptional activity results from double site occupancy (that is two DP-1/E2F-1 heterodimers), rather than because of any direct contribution from orf 6/7. It is therefore suggested that orf 6/7 functions predominantly as a virally encoded dimerization domain which is specific for DRTF1/E2F DNA binding activities, such as the DP-1/E2F-1 heterodimer.

During adenovirus lytic infection at least two virus-directed mechanisms will usurp the normal regulation of DRTF1/E2F. First, the Ela protein sequesters, and presumably inactivates, proteins such as pRb which normally repress the transcriptional activity of DRTF1/E2F. Transcriptionally active DRTF1/E2F is then able to activate cellular genes, some of which encode proteins necessary for viral replication. Second, the orf 617 protein targets this single E2F site activity, composed of DPIE2F heterodimers, converting it into a form which preferentially recognises the organisation of sites which occur in viral promoters, such as E2a (whose gene encodes a viral protein necessary for replication), thus maintaining the expression of essential viral genes during the viral replication cycle.

In summary, it has been shown that DP-1 is a frequent component of DRTF1/E2F in 3T3 cells and that its level of phosphorylation is under cell cycle control. Furthermore, the presence of DP-1 in DRTF1/E2F enhances the interaction with pRb and is functionally crucial for recognition by the orf 6/7 protein. DP-1 therefore plays a crucial role in enabling viral and cellular proteins to interact with DRTF1/E2F.

Preparation of extracts from cell lines, gel retardation, and immunochemical techniques:

Extracts were prepared as previously described (Partridge and La Thangue, 1991). Gel retardation reactions were performed using either an oligonucleotide which contained the distal E2F binding site taken from the adenovirus type 5 E2a promoter (nucleotides −71 to −50) or the complete wildtype E2a promoter (nucleotides −96 to +68) which contains two E2F sites. Addition of the antisera and competing peptides (about 2n moles for the DP-1 peptide) was as previously described (Girling et al., 1993). Immunoblotting was performed by standard procedures and affinity purified anti DP-1 (A) was used for immunoblotting. Affinity purification was performed using a peptide A affinity matrix in which peptide A was coupled to cyanogen bromide activated Sepharose CL4B. The other antibodies used were anti DP-1(D), SD15 for anti p107 (Dyson et al., 1993), 134 for anti-E2F-1 (Bandara et al., 1993), a rabbit polyclonal anti-orf 6/7 (Bocco et al., 1993), and a rabbit polyclonal anti-cyclin A (Bandara et al., 1991). Either pre-immune sera or an unrelated monoclonal antibody were used as controls. DRTF1/E2F DNA binding activity was affinity purified exactly as previously described by repeat application to an E2F binding site affinity matrix (Girling et al., 1993). Dephosphorylation of cell extracts was performed by adding human placental phosphatase (4.0U), potato acid phosphatase (1.2U) and calf intestinal phosphatase (20U), followed by incubation at 37° C. for 40 min; control treatments lacked phosphatase. Extracts were subsequently immunoblotted with anti-DP-1(A).

Fusion proteins and in vitro translation:

DP-1, E2F-1, pRb, pRbA22 and pRb C→F 706 were expressed as GST fusion proteins and purified as described (Bandara et al., 1993;Girling et al., 1993). DP-1, E2F-1, E1a and CREBP1 (Maekawa et al., 1989) coding sequences were transcribed and translated using reticulocyte lysate (Promega; Bandara et al., 1993), and the orf 6/7 protein was expressed and purified as previously described (Bocco et al., 1993) and was kindly provided by Jose Bocco and Claude Kedinger. In the protein binding assay (FIG. 4), polypeptides were translated and radiolabelled with $^{35}$S methionine and incubated with the appropriate GST fusion protein for 30 min at 30° C., collected with glutathione-agarose (Sigma) and washed repeatedly with 0.1% NP40 in PBSA. Bound proteins were released by denaturation in SDS sample buffer and resolved in a 10% polyacrylamide gel as previously described (I3andara et al., 1993). The efficiency of translation was assessed for each polypeptide. Δ341 and Δ327 were created by digesting pGDP-1 (Bandara et al., 1993) with Bam HI and Kpnl respectively. A73–340 was made by polymerase chain reaction using a 5' oligonucleotide incorporating an efficient ribosome binding site. Δ211 was made by exonuclease III digestion of the DP-1 cDNA from the 3' terminus using the Promega Erase-a-Base system.

Metabolic radiolabelling:

F9 EC cells (about 1×10$^6$) were radiolabellled for 4 h with 3 mCi of $^{32}$P-orthophosphate (Amershain International) and harvested in lysis buffer (50 mnM Tris-HCl pH8.0, 155 mM NaCl, 0.1% NP40, 2 μg/ml Aprotonin, 0.5 mM PMSF). Cell lysate was immunoprecipitated in two steps with two different anti-DP-1 antibodies. First, anti-DP-1 (A) in the presence of either the homologous peptide (peptide A; 2 nmole) or an unrelated peptide (peptide 1, 2nmole) was added to the radiolabelled lysate for 1 h, after which protein A Sepharose beads (Pharmacia) were added and incubated for a further 1 h. The Sepharose beads were harvested and repeatedly washed with lysis buffer. Proteins immunoprecipitated with anti-DP-1 (A) were released by adding the homologous peptide (peptide A (residues 3 to 15 of DP-1); 2 nmole) to the immunoprecipitate performed in the presence of the unreleated peptide (peptide 1). Re-immunoprecipitation of released proteins was performed with anti-DP-1 (D) in the presence of either the homologous peptide (peptide D; 2 nmole) or the unrelated peptide (peptide 1; 2 nmole). The reaction was incubated for 1 h, after which protein A Sepharose beads were added and incubated for a further 1 h. Bound proteins were resolved by SDS gel electrophoresis. For the analysis of DRTF1/E2F DNA binding activity, immunoprecipitates were treated with gel retardation buffer (containing either homologous or unrelated peptide; 2 nmole) and thereafter assayed for DNA binding activity to the E2F site in the presence of competing mutant E2F site.

Transfection of Drosophila tissue culture cells:

Reporter constructs p3xWT and p3xMT have been previously described (Zamanian and La Thangue, 1992). pE2a contains wild-type E2a promoter sequences (−96 to +68) driving the CAT gene and has been previously described (SivaRaman and Thimmappaya, 1987). pDP-1 and pE2F-1 contain complete DP-1 and E2F-1 proteins (Bandara et al., 1993). pE4 contains a complete Ad5 orf 6/7 cDNA regulated by the E4 promoter and was kindly provided by Claude Kedinger. Transfections and CAT assays were performed as previously described (Bandara et al., 1993).

Cell cycle analysis:

For the cell cycle analysis (FIG. 2), NIH 3T3 cells were cultured for 36 h in medium (DMEM) containing 0.1% fetal calf serum (FCS). Subsequently, each culture was washed and DMEM containing 10% FCS added, cells being harvested at the appropriate times (every 4 h) thereafter. Cells were assessed for DNA synthesis using the Cell Proliferation Kit (Amersham International) according to the manufacturer's instructions. Briefly, cells were grown on sterile coverslips in the presence of bromodeoxyuridine (BrdU) and, at the appropriate time intervals, coverslips were removed and immunostaining with anti-BrdU performed as recommended by the manufacturer. Parallel cultures were prepared for analysis by gel retardation and immunoblotting. In this cell system, DNA synthesis began at 8 h and peaked at about 12 h post-serum stimulation. Cells began to divide at about 20 h post serum stimulation.

REFERENCES

Bagchi, S., Raychaudhuri, P. and Nevins, J. R. (1990) Cell 62, 659–669.

Bandara, L. R. and La Thangue, N. B. (1991) Nature 351, 494–497.

Bandara, L. R., Adamczewski, J. P., Hunt, T. and La Thangue, N. B. (1991) Nature 352, 249–251.

Bandara, L. R., Adamczewski, J. P., Poon, R. Y., Zamanian, M., Hunt, T. and La Thangue, N. B. (1992) J. Cell Sci. 16, 77–85.

Bandara, L. R., Buck, V. M., Zamranian, M., Johnston, J. H. and La Thangue, N. B. (1993) EMBO J. 12, 4317–4324.

Blake, M. C. and Azizkhan, J. C. (1989) Mol. Cell. Biol. 9, 4994–5002.

Bocco, J. L., Reimund, B., Chatton, B. and Kedinger, C. (1993) Oncogene 8, 2977–2986.

Chellappan, S. P., Hiebert, S. W., Mudryj, M., Horowitz, J. M. and Nevins, J. R. (1991) Cell 65, 1053–1061.

Chittenden, T., Livingston, D. M. and DeCaprio, J. A. (1993). Mol. Cell. Biol. 13, 3975–3983.

Dalton, S. (1992) EMBO J. 11, 1797–1804.

Devoto, S. H., M. Mudryj, P. Pines, T. Hunter and J. R. Nevins. (1992). A cyclin A-specific protein kinase complex possesses sequence-specific DNA binding activity: p33cd1 is a component of the E2F-cyclin A complex. Cell 68:167–176.

Dyson. N., Dembski. M., Fattaey, A., Ngwu, C., Ewen, M. and Helin, K. (1993). J. Virol. 67, 7641–7647.

Girling, R., Partridge, J. F., Bandara, L. R., Burden, N., Totty, N., Hsuan, J. J. and La Thangue, N. B. (1993) Nature 362, 83–87.

Hardy, S. and Shenk, T. (1989) Mol. Cell. Biol. 9, 4495–4506.

Heibert, S. W., Chellappan, S. P., Horowitz, J. M. and Nevins, J. R. (1992) Genes Dev. 6, 177–185.

Helin, K., Lees, J. A., Vidal, M., Dyson, N., Harlow, E. and Fattaey, A. (1992) Cell 70, 337–350.

Helin, K., Wu, C. L., Fattaey, A. R., Lees, J. A., Dynlacht, B. D., Ngwu, C. and Harlow, E. (1993). Genes Dev. 7, 1850–1861.

Hu, Q., Dyson, N. and Harlow, E. (1990). EMBO J. 9, 1147–1155.

Hu, Q., Bautista, C., Edwards, G. DefeoJones, D., Jones, R. and Harlow, E. (1991). Mol. Cell. Biol. 11, 5792–5799

Huang, M. M. and Hearing, P. (1989) Genes Dev. 3, 1699–1710.

Ivey-Hoyle, M., Conroy, R., Huber, H., Goodhart, P., Oliff, A. and Heimbrook, D. C. (1993) Mol. Cell. Biol. 13, 7802–7812.

Kaelin. W. G., Krek, W., Sellers, W. R., DeCaprio, J. A., Ajchenbaum, F., Fuchs, C. S., Chittenden, T., Li, Y., Farnhim, P. J., Blanar, M. A., Livingston, D. M. and Flemington, E. K. (1992) Cell 70, 351–364.

La Thangue, N. B. and Rigby, P. W. J. (1987) Cell 49, 507–513.

La Thangue, N. B. (1994). Trends Biochem. Sci. 19, 108–114.

Lees, E., Faha, B., Dulic, V., Reed, S. I. and Harlow, E. Genes Dev. (1992) 7, 1850–1861.

Lees, J. A., Saito, M., Vidal, M., Valentine, M., Look, T., Harlow. E., Dyson, N. and Helin, K. (1993). Mol. Cell. Biol. 13, 7813–7825

Marton. M. J., Baim, S. B., Ornelles, D. A. and Shenk, T. (1990). J. Virol. 64, 2345–2359.

Maekawa, T., Sakura, H., Kanei-Ishii, C., Sudo, T., Yoshimura, T., Fujisawa, J., Yoshida, M. and Ishii, S. (1989). EMBO J. 8, 2023–2028

Means, A. L., Slansky, J. E., McMahon, S. L., Knuth, M. W. and Farnham, P. J. (1992) Mol. Cell Biol. 12, 1054–1063.

Mudryj, M., Devoto, S. H., Hiebert, S. W., Hunter, T., Pines, J. and Nevins, J. R. (1991) Cell 65. 1243–1253.

Nevins. J. R. (1992) Science 258, 424429.

Partridge, J. F. and La Thangue, N. B. (1991) EMBO J. 10, 3819–3827.

Raychaudhuri, P., Bagchi, S. D., Neill, S. & Nevins, J. R. (1990) J. Virol. 64, 2702–2710.

Schwartz, J. K., Devoto, S. H., Smith, E. J., Chellappan, S. P., Jakoi, L. and Nevins, J. R. (1993) EMBO J. 12, 1013–1020.

Shan, B., Zhu, X., Chen, P. L., Durfee, T., Yang, Y., Sharp, D. and Lee, W. H. (1992) Mol. Cell. Biol. 12, 5620–5631.

Shirodkar, S., Ewen, M., DeCaprio, J. A., Morgan, J., Livingston, D. M. and Chittenden, T. (1992) Cell 68, 157–168.

SivaRaman, L. and ThimInappaya, B. (1987). Proc. Natl. Acad. Sci. U.S.A. 84, 6112–6116.

Zamanian, M. and La Thangue, N. B. (1992) EMBO J. 11, 2603–2610.

Zamanian, M. and La Thangue, N. B. (1993) Mol. Biol. Cell. 4, 389–396.

I claim:

1. An assay for a potential growth prevention, inhibiting or enhancing agent, the assay comprising:
   (i) bringing the agent into contact with a cell containing a DP protein; and
   (ii) measuring the phosphorylation state of the DP protein.

2. An assay for a potential growth prevention, inhibiting or enhancing agent, the assay comprising:
   (i) providing an extract from a cell which contains a DP protein in a hypophosphorylated state;
   (ii) bringing the extract into contact with the agent; and
   (iii) measuring the phosphorylation state of the DP protein.

3. An assay for a potential growth prevention, inhibiting or enhancing agent the assay comprising:
   (i) providing an extract from a cell which contains a DP protein in a phosphorylated state;
   (ii) bringing the extract into contact with the agent; and
   (iii) measuring the phosphorylation state of the DP protein.

4. An assay for a potential DP protein phosphorylation modulating agent, the assay comprising:
   (i) contacting a medium which contains a DP protein in a hypophosphorylated or phosphorylated state and a phosphorylating or dephosphorylating enzyme with the agent; and
   (ii) measuring the phosphorylation state of the DP protein.

5. An assay according to claim 1 wherein measurement of the DP protein phosphorylation state comprises measuring the amount of $^{32}P$ in the DP protein or measuring the mobility of the DP protein on a SDS/polyacrylamide gel.

6. An assay according to claim 2 wherein measurement of the DP protein phosphorylation state comprises measuring the amount of $^{32}P$ in the DP protein or measuring the mobility of the DP protein on a SDS/polyacrylamide gel.

7. An assay according to claim 3 wherein measurement of the DP protein phosphorylation state comprises measuring the amount of $^{32}P$ in the DP protein or measuring the mobility of the DP protein on a SDS/polyacrylamide gel.

8. An assay according to claim 4 wherein measurement of the DP protein phosphorylation state comprises measuring the amount of $^{32}P$ in the DP protein or measuring the mobility of the DP protein on a SDS/polyacrylamide gel.

9. An assay according to claim 1 wherein measurement of the DP protein phosphorylation state comprises measuring the extent of binding of said protein to an antibody which binds to the C-terminal region of said protein more strongly when said protein is hypophosphorylated than when it is phosphorylated.

10. An assay according to claim 2 wherein measurement of the DP protein phosphorylation state comprises measuring the extent of binding of said protein to an antibody which binds to the C-terminal region of said protein more strongly when said protein is hypophosphorylated than when it is phosphorylated.

11. An assay according to claim 3 wherein measurement of the DP protein phosphorylation state comprises measuring the extent of binding of said protein to an antibody which binds to the C-terminal region of said protein more strongly when said protein is hypophosphorylated than when it is phosphorylated.

12. An assay according to claim 4 wherein measurement of the DP protein phosphorylation state comprises measuring the extent of binding of said protein to an antibody which binds to the C-terminal region of said protein more strongly when said protein is hypophosphorylated than when it is phosphorylated.

* * * * *